US007723046B2

(12) United States Patent
Maruyama et al.

(10) Patent No.: US 7,723,046 B2
(45) Date of Patent: May 25, 2010

(54) METHOD OF SCREENING FOR A COMPOUND USING GUANOSINE TRIPHOSPHATE (GTP)-BINDING PROTEIN-COUPLED RECEPTOR PROTEIN, BG37

(75) Inventors: Takaharu Maruyama, Ibaraki (JP); Takao Nakamura, Ibaraki (JP); Haraku Itadani, Ibaraki (JP); Ken-ichi Tanaka, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 428 days.

(21) Appl. No.: 11/704,546

(22) Filed: Feb. 8, 2007

(65) Prior Publication Data
US 2007/0141642 A1 Jun. 21, 2007

Related U.S. Application Data

(62) Division of application No. 10/432,101, filed as application No. PCT/JP01/09512 on Oct. 30, 2001, now Pat. No. 7,198,914.

(30) Foreign Application Priority Data

Nov. 17, 2000 (JP) .............................. 2000-351741
Feb. 15, 2001 (JP) .............................. 2001-38619
Mar. 16, 2001 (JP) .............................. 2001-77000

(51) Int. Cl.
G01N 33/53 (2006.01)
C07K 14/00 (2006.01)

(52) U.S. Cl. ...................... 435/7.1; 435/69.1; 536/23.5; 530/350

(58) Field of Classification Search ........................ None
See application file for complete search history.

(56) References Cited

U.S. PATENT DOCUMENTS

| 5,858,716 | A | * | 1/1999 | Elshourbagy et al. ...... 435/69.1 |
| 6,475,753 | B1 | | 11/2002 | Ruben et al. |
| 6,783,969 | B1 | | 8/2004 | Tang et al. |
| 2002/0119493 | A1 | | 8/2002 | Glucksmann |

FOREIGN PATENT DOCUMENTS

| EP | 1273659 | 1/2003 |
| WO | WO 99/66041 | 12/1999 |
| WO | WO 00/39164 | 7/2000 |
| WO | WO 00/58462 | 10/2000 |
| WO | WO 01/46414 | 6/2001 |
| WO | WO 01/77325 | 10/2001 |
| WO | WO 02/08258 A2 | 1/2002 |
| WO | WO 02/10387 A | 2/2002 |
| WO | WO 02/16548 A | 2/2002 |
| WO | WO 02/072823 A2 | 9/2002 |
| WO | WO 02/084286 A | 10/2002 |
| WO | WO 02/088355 A | 11/2002 |

OTHER PUBLICATIONS

Weigel, Biochem. J., 319: 657-667, 1996.*
Supplementary Partial European Search Report from corresponding European Patent Application Serial No. 01 97 6875.
Houten, S.M. (2006) "New EMBO member's review: endocrine functions of bile acids" *The EMBO Journal* 25:1419-1425.
Katsuma, S. (2005) "Bile acids promote glucagon-like peptide-1 secretion through TGR5 in a murine enteroendocrine cell line STC-1" *Biochemical and Biophysical Research Communications* 329:386-390.
Kawamata, Y. et al. (2003) "A G protein-coupled receptor responsive to bile acids" *The Journal of Biological Chemistry* 278:9435-9440.
Watanabe, M. et al. (2006) "Bile acids induce energy expenditure by promoting intracellular thyroid hormone activation" *Nature* 439:484-489.
The Sanger Center (1998) "Toward a complete human genome sequence," *Genome Research*, 8:1097-1108.
Bonaldo, et al. (1996) "Normalization and subtract: two approaches to facilitate gene discovery" *Genome Research* 6:791-806.
Bowie et al. (1990) "Deciphering the message in protein sequences: tolerance to amino acid substitutions" *Science* 247:1306-1310.
Wells, J.A. (1990) "Additivity of mutation effects in proteins" *Biochemistry* 29:8509-8517.
Wang, A. et al. (1999) Rapid analysis of gene expression (RAGE) facilitates universal expression profiling *Nucleic Acids Research* 27:4609-4618.
Campbell, K. et al. (1997) "Totipotency or multipotentiality of cultured cells: applications and progress" *Theriogenology* 47:63-72.
Philipps, A. (2001) "The challenge of gene therapy and DNA delivery" *Journal of Pharmacy and Pharmacology* 53:1169-1174.
Maruyama, T. et al. (2002) Identification of membrane-type receptor for bile acids (M-BAR) *Biochemical and Biophysical Research Communications* 298:714-719.
Wigley, P. et al. (1994) "Site-specific transgene insertion: an approach" *Reprod. Fertil. Dev.* 6:585-588.

* cited by examiner

*Primary Examiner*—Robert Landsman
*Assistant Examiner*—Gyan Chandra
(74) *Attorney, Agent, or Firm*—John D. Reilly; John C. Todaro

(57) ABSTRACT

The present inventors conducted a similarity search of the amino acid sequence of known G protein-coupled receptor proteins in GenBank, and obtained a novel human GPCR gene "BG37". cDNA containing the ORF of the gene was cloned and its nucleotide sequence was determined. Moreover, novel GPCR "BG37" genes from mouse and rat were isolated. Use of the novel GPCR of the present invention enables screening of ligands, compounds inhibiting the binding to a ligand, and candidate compounds of pharmaceuticals which can regulate signal transduction from the "BG37" receptor.

3 Claims, 6 Drawing Sheets

METHOD OF SCREENING FOR A COMPOUND USING GUANOSINE TRIPHOSPHATE (GTP)-BINDING PROTEIN-COUPLED RECEPTOR PROTEIN, BG37

RELATED APPLICATIONS

This application is a divisional of U.S. patent application Ser. No. 10/432,101, filed Dec. 11, 2003, which is now U.S. Pat. No. 7,198,914 and which is a U.S. National Phase of International Application No. PCT/JP01/09512, filed on Oct. 30, 2001, which claims the benefit of Japanese Application Serial No. 2001-77000, filed Mar. 16, 2001, Japanese Application No. 2001-38619, filed Feb. 15, 2001, and Japanese Application No. 2000-351741, filed Nov. 17, 2000.

TECHNICAL FIELD

The present invention relates to novel guanosine triphosphate-binding protein-coupled receptor proteins, DNAs encoding the proteins, and a method of screening for candidate compounds for pharmaceuticals using the same.

BACKGROUND ART

Many hormones and neurotransmitters regulate biological functions via specific receptor proteins existing on the cell membrane. Most of such receptor proteins achieve intracellular signaling via the activation of coupled guanosine triphosphate-binding proteins (hereinafter abbreviated as "G proteins"). Thus, the receptor proteins are collectively called "G protein-coupled receptor proteins", or "seven-transmembrane receptor proteins", due to their common structure comprising seven transmembrane domains.

G protein-coupled receptor proteins exist on the surface of living cells and various functional cells in organs. The receptor proteins play exceedingly important roles as targets of various molecules, for example, such as hormones, neurotransmitters, and physiologically active substances, that regulate the functions of the cells and organs.

An exemplary pathway wherein a hormone or neurotransmitter and a G protein-coupled receptor regulate biological function includes the hypothalamic pituitary system. In this system, the secretion of pituitary hormones from pituitary is regulated by the function of hypothalamic hormones, and the pituitary hormones released into blood regulate the functions of target cells and organs. For example, functions important for the living body, such as maintenance of homeostasis, and development and/or growth of genital system and individuals, are regulated via the pathway.

Representative hypothalamic hormones include thyrotropin-releasing hormone (TRH), corticotropin-releasing factor (CRF), growth hormone-releasing factor (GRF), and somatostatin; and pituitary hormones include thyroid stimulating hormone (TSH), adrenocorticotropic hormone (ACTH), follicle stimulating hormone (FSH), luteinizing hormone (LH), prolactin, growth hormone, oxytocin, and vasopressin. In particular the secretion of pituitary hormones is regulated by a positive or negative feedback mechanism by hypothalamic hormones and peripheral hormones secreted from target endocrine gland.

These hormones and their receptors are known to be present not only in the hypothalamic pituitary system but also are widely distributed in the brain. The hormones and their receptors are also similarly distributed in peripheral tissues and are believed to perform important functions.

For example, pancreas plays an important role in sugar metabolism via the secretion of glucagon and insulin in addition to digestive juice. Insulin is secreted from β cells of the pancreas, which secretion is mainly promoted by glucose. However, various types of receptors are present on the β cells, and, in addition to glucose, insulin secretion is known to be controlled by various factors, such as peptide hormones (galanin, somatostatin, gastrin, secretin, gastric inhibitory polypeptide, glucagon, etc.), sugars (mannose, etc.), amino acids, and neurotransmitters.

In digestive organs, such as the stomach and small intestine, food digestion and absorption are performed by the secretion of various digestive juices under the control of multiple hormones, hormone-like substances, neurotransmitters or physiologically active substances including gastrin, secretin, glucagon, gastrin-releasing peptide, vasoactive intestinal peptide, acetylcholine, noradrenaline, and serotonin. The secretion of these substances is believed to be regulated by receptors corresponding to each substance existing in stomach, small intestine, and so on.

Similarly, in the cardiovascular system and respiratory system such as the heart and lung, the contraction and relaxation of cardiac muscle and vascular smooth muscle, the control of blood pressure, and such are strictly performed under the regulation of neurotransmitters, hormones, physiologically active substances, etc.

As described above, in peripheral tissues, such as brain and pituitary, receptor proteins of various hormones and neurotransmitters exist and play important roles in regulating the functions of the tissues. Thus, G protein-coupled receptor proteins have been greatly attracting attention as targets to develop pharmaceuticals.

Previously reported G protein-coupled receptor proteins include: muscarinic acetylcholine receptors M1, M2, M3, and M4 (Peralta, E. G. et al., EMBO J. 6, 3923-3929 (1987)); muscarinic acetylcholine receptor M5 (Bonner, T. I. et al., Neuron 1, 403-410 (1988)); adenosine receptor A1 (Libert, F. et al., Science 244, 569-572 (1989)); α1A adrenoreceptor (Bruno, J. F. et al., Biochem. Biophys. Res. Commun. 179, 1485-1490 (1991)); β1 adrenoreceptor (Frielle, T. et al., Proc. Natl. Acad. Sci. USA 84, 7920-7924 (1987)); angiotensin receptor AT1 (Takayanagi, R. et al., Biochem. Biophys. Res. Commun. 183, 910-916 (1992)); endothelin receptor ETA (Adachi, M. et al., Biochem. Biophys. Res. Commun. 180, 1265-1272 (1991)); gonadotropin-releasing factor receptor (Kaker, S. S. et al., Biochem. Biophys. Res. Commun. 189, 289-295 (1992)); histamine receptor H2 (Ruat, M. et al., Proc. Natl. Acad. Sci. USA 87, 1658-1672 (1992)); neuropeptide Y receptor Y1 (Larhammar, D. et al., J. Biol. Chem. 267, 10935-10938 (1992)); interleukin 8 receptor IL8RA (Holmes, W. E. et al., Science 2563, 1278-1280 (1991)); dopamine receptor D1 (Mahan, L. C. et al., Proc. Natl. Acad. Sci. USA 87, 2196-2200 (1990)); metabolic glutamate receptor mGluR1 (Masu, M. et al., Nature 349, 760-765 (1991)); somatostatin receptor SS1 (Yamada, Y. et al., Proc. Natl. Acad. Sci. USA 89, 251-255 (1992)), etc. (see, Watson, S. and Arkinstall, S., The G-Protein Linked Receptor FactsBook, Academic Press (1994)). Furthermore, already developed pharmaceuticals targeting a G protein-coupled receptor protein include: terazosin hydrochloride (antihypertensive agent, α1 adrenoreceptor antagonist), atenolol (antiarrhythmic agent, β1 adrenoreceptor antagonist), dicyclomine hydrochloride (anticonvulsant, acetylcholine receptor antagonist), ranitidine hydrochloride (peptic ulcer agent, histamine receptor H2 antagonist), trazodone hydrochloride (antidepressant, serotonin receptor 5-HT1B antagonist), buprenorphine hydrochloride (analgesic, opioid receptor κ agonist), etc. (see, Stadel. J.

M. et al., Trends Pharm. Sci. 18, 430-437 (1997); Pharmaceutical Catalogue, 5th ed., Jiho, Inc.).

DISCLOSURE OF THE INVENTION

An objective of the present invention is to provide novel G protein-coupled receptor proteins, DNAs encoding the proteins, a method for producing the G protein-coupled receptor proteins and a method for using the proteins and DNAs.

The present inventors intensively studied to achieve the above objective. First, the present inventors searched the GenBank high throughput genomic division for similarity among approximately 400 known G protein-coupled receptor protein (GPCR) amino acid sequences to identify candidates for novel GPCR genes. The inventors prepared a list of sequences obtained by the search, which sequences exhibited similarity to known GPCRs, and then carried out similarity searches of the nucleotide sequences on database of known GPCRs. The inventors examined whether the nucleotide sequences were identical to any of known GPCRs, and, when not identical, confirmed the degree of similarity to obtain novel GPCR candidate sequences. AC021016 was found as one of such candidates, and was dubbed human "BG37".

Next, the present inventors amplified a 414-bp fragment of AC021016 and carried out 3'-RACE to amplify and obtain its sequence information on the C-terminus of the fragment. The newly identified nucleotide sequence was assembled with the already obtained fragment, human "BG37", and the resulting sequence was searched for similarity on the GenBank high throughput genomic division. The search revealed AC055884, a nucleotide sequence identical to the above-identified sequence. AC055884 and AC021016 shared a common sequence except for a single nucleotide gap. The initiation codon of human "BG37" was found based on the nucleotide sequence information of AC055884 and AC021016, and the open reading frame (ORF) of human "BG37" was estimated to consist of 993 bp.

Then, the present inventors cloned a cDNA containing the ORF of human "BG37" and determined its nucleotide sequence. The deduced amino acid sequence of a protein encoded by the human "BG37" gene was found to consist of 330 amino acid residues. According to a motif analysis, the protein was predicted to be a seven-transmembrane receptor.

Furthermore, to analyze the expression patterns of the gene, the present inventors carried out Northern hybridization using RNAs from human tissues. Human "BG37" was revealed to be expressed in heart, skeletal muscle, spleen, kidney, liver, small intestine, placenta, lung, and peripheral blood leukocyte. The finding that human "BG37" was expressed in various tissues suggested functional importance of the gene in human.

Then, the present inventors searched for ligands of the receptor protein encoded by the human "BG37" gene. First, a cell expressing human "BG37" protein at a high level was prepared, a test compound was contacted with the cell, and intracellular cAMP level was measured. The result showed that biological steroid hormones, including progesterone, dehydroisoandrosterone, testosterone, androstenedione, pregnenolone, and 5α-dihydrotestosterone, increased the intracellular cAMP level in a concentration-dependent manner. Thus, steroid hormones, including progesterone, were revealed to specifically increase the intracellular cAMP level via the "BG37" receptor protein.

The present inventors also succeeded in isolating a mouse analog to "BG37". The ORF of this gene was 990 by in length and was estimated to encode a protein consisting of 329 amino acids. The mouse "BG37" was confirmed to have a homology of 83% and 84% to the human "BG37" at the nucleotide sequence and amino acid sequence level, respectively. Furthermore, expression analyses revealed the expression of mouse "BG37" in heart, spleen, lung, liver, skeletal muscle, kidney, and testis, as well as in day-7, -11, -15, and -17 mouse embryos.

The present inventors further succeeded in isolating a rat analog to "BG37". The ORF of this gene was 990 by in length and was estimated to encode a protein consisting of 329 amino acids. The rat "BG37" was confirmed to exhibit 84% and 82% homology to the human "BG37" at the nucleotide sequence and amino acid sequence level, respectively. Furthermore, expression analyses of the gene revealed the rat "BG37" to be expressed in lung, liver, and kidney.

As described above, the present inventors discovered the novel gene "BG37," which was believed to encode a G protein receptor protein, and completed the present invention. The "BG37" protein of the present invention can be preferably used, for example, using its binding activity as an indicator, to screen for ligands, compounds which inhibit the binding with such ligands, and candidate compounds for pharmaceuticals which can regulate the signal transduction via the "BG37" protein.

Thus, the present invention relates to novel G protein-coupled receptor proteins, DNAs encoding the proteins, and a screening method for candidate compounds for ligands and pharmaceuticals using the proteins. More specifically, the present invention provides:

[1] A DNA encoding a guanosine triphosphate-binding protein-coupled receptor protein selected from the group of:

(a) a DNA encoding a protein comprising the amino acid sequence of SEQ ID NO: 2, 20 or 38;

(b) a DNA containing the coding region of nucleotide sequence of SEQ ID NO: 1, 19 or 37;

(c) a DNA encoding a protein comprising the amino acid sequence of SEQ ID NO: 2, 20 or 38, wherein the amino acid sequence comprises one or more amino acid substitutions, deletions, additions and/or insertions; and (d) a DNA hybridizing under a stringent condition to the DNA consisting of the nucleotide sequence of SEQ ID NO: 1, 19 or 37;

[2] a DNA encoding a partial peptide of a protein consisting of the amino acid sequence of SEQ ID NO: 2, 20 or 38;

[3] the protein or peptide encoded by the DNA according to [1] or [2];

[4] a vector containing the DNA according to [1] or [2];

[5] a transformant containing the DNA according to [1] or [2], or the vector according to [4];

[6] a method for producing the protein or peptide according to [3], which comprises the steps of: culturing the transformant according to [5], and collecting the expressed protein or peptide;

[7] an antibody which binds to the protein or peptide according to [3];

[8] a polynucleotide of at least 15 nucleotides, which hybridizes to the DNA consisting of the nucleotide sequence of SEQ ID NO: 1, 19 or 37;

[9] a method of screening for a ligand or an analog thereof, which binds to the protein according to [3], said method comprising the steps of:

(a) contacting a test compound with the protein or peptide according to [3]; and (b) selecting the compound which binds to the protein or peptide;

[10] a method of screening for a compound having the activity to inhibit the binding between the protein according to [3] and its ligand or an analog thereof, said method comprising the steps of:

(a) contacting a ligand or analog thereof with the protein or peptide according to [3] in the presence of a test compound, and detecting the binding activity of the protein or peptide to the ligand or analog thereof;

(b) selecting the compound which decreases the binding activity detected in step (a) compared to that detected in the absence of the test compound;

[11] a method of screening for a compound which inhibits or enhances the activity of the protein according to [3], which comprises the steps of:

(a) contacting a cell that expresses the protein with a ligand of the protein or an analog thereof in the presence of a test compound;

(b) detecting alteration in the cell caused by the binding of the protein with the ligand or analog thereof; and (c) selecting the compound which suppresses or enhances the alteration in the cell detected in step (b), compared to that in the cell in the absence of the test compound;

[12] the method of screening according to [10] or [11], wherein the ligand is a biological substance having the steroid backbone;

[13] the method of screening according to [12], wherein the biological substance having the steroid backbone is selected from the group consisting of progesterone, dehydroisoandrosterone, testosterone, androstenedione, pregnenolone, cholic acid, chenodeoxycholic acid, deoxycholic acid, lithocholic acid, ursodeoxycholic acid, and 5α-dihydrotestosterone;

[14] a kit for screening according to any one of [9] to [13], which comprises the protein or peptide according to [3];

[15] a compound isolated by the screening according to any one of [9] to [13]; and

[16] a pharmaceutical composition comprising as an active ingredient the compound according to [15].

As used herein, the term "G protein-coupled receptor protein" refers to a receptor protein which performs intracellular signaling via the activation of a G protein. Herein, the term "ligand" refers to a natural compound which binds to a G protein-coupled receptor protein and has the activity of inducing signal transduction. In addition, as used herein, the term "agonist" refers to a compound having a physiological activity similar to that of a ligand of a G protein-coupled receptor protein, and includes both natural and artificially synthesized compounds. Furthermore, as used herein, the term "antagonist" refers to a compound having the activity to suppress the physiological activity of a ligand of a G protein-coupled receptor protein, and includes both natural and artificially synthesized compounds. In addition, herein, the terms "protein" and "peptide" include their salts.

The present invention relates to a novel G protein-coupled receptor protein (GPCR). The nucleotide sequence of the cDNA of the human G protein-coupled receptor protein "BG37" (human "BG37") isolated by the present inventors is shown in SEQ ID NO: 1, and the amino acid sequence of the "BG37" protein encoded by the cDNA is shown in SEQ ID NO: 2. In addition, the nucleotide sequence of the cDNA of the mouse G protein-coupled receptor protein "BG37" (mouse "BG37") is shown in SEQ ID NO: 19, and the amino acid sequence of "BG37" protein encoded by the cDNA is shown in SEQ ID NO: 20. Furthermore, the nucleotide sequence of the cDNA of the rat G protein-coupled receptor protein "BG37" (rat "BG37") is shown in SEQ ID NO: 37, and the amino acid sequence of "BG37" protein encoded by the cDNA is shown in SEQ ID NO: 38. As used herein, the term "BG37" refers to all of human "BG37", mouse "BG37", and rat "BG37", unless otherwise stated.

The human, mouse, and rat "BG37" proteins of the present invention contain open reading frames encoding proteins of 330, 329, and 329 amino acid residues, respectively. Hydropathy plot analysis showed that the human "BG37" protein has seven hydrophobic domains characteristic of G protein-coupled receptor proteins (FIG. 1).

Thus, the "BG37" protein was predicted to be a seven-transmembrane receptor. Furthermore, signal indicating the expression of receptor mRNA encoded by the human "BG37" gene was detected among human tissues, including heart, skeletal muscle, spleen, kidney, liver, small intestine, placenta, lung, and peripheral blood leukocyte. Among mouse tissues, the expression of the mouse "BG37" protein was confirmed in heart, spleen, lung, liver, skeletal muscle, kidney, and testis, as well as in day-7, -11, -15, and -17 embryos. Among rat tissues, lung, liver, and kidney were confirmed to express the rat "BG37" protein. Furthermore, ligands for the human "BG37" were revealed to include biological steroid hormones, such as progesterone, dehydroisoandrosterone, testosterone, androstenedione, pregnenolone, and 5α-dihydrotestosterone.

These findings show that the "BG37" protein belongs to the family of G protein-coupled receptor proteins and is important for human, mouse, and rat. Furthermore, due to the fact that the "BG37" protein is a G protein-coupled receptor protein, the protein is suggested to perform signal transduction via G protein activation through its ligand.

A protein of the present invention can be used to screen for a ligand which, in turn, can be used as a pharmaceutical or a compound which inhibits the binding to the ligand.

A biological substance having a steroid backbone is preferably used as a ligand for a receptor protein of the present invention. Such biological substances include biological steroid hormones, including progesterone, dehydroisoandrosterone, testosterone, androstenedione, pregnenolone, and 5α-dihydrotestosterone, which were identified by the present inventors. Furthermore, such substances also include bile acids, such as cholic acid, chenodeoxycholic acid, deoxycholic acid, lithocholic acid, and ursodeoxycholic acid. The bile acids may be in a form of conjugates, such as glycine conjugates or taurine conjugates. Additional potential ligands include, but are not limited to, parathormone (PTH), calcitonin, calcitonin gene-related protein (CGRP), glucagon, secretin, adrenomedullin, serotonin, adrenalin, noradrenaline, galanin, somatostatin, chemokine, and histamine.

Abnormalities in signal transduction via a protein of the present invention can be the cause of various diseases. Thus, a compound which activates or suppresses the G protein-coupled receptor of the present invention is expected to be applicable as a pharmaceutical. Target diseases to be treated or prevented with a compound which activates or suppresses the G protein-coupled receptor of the present invention include, for example, the following diseases:

heart diseases: cardiac arrhythmia, heart failure, cardiomyopathy, cardiac valve diseases, heart tumor, endocarditis, pericardial diseases, hypotension, hypotensive shock, hypertension, atherosclerosis, coronary artery diseases, peripheral artery diseases, etc.;

lung diseases: acute respiratory distress syndrome, pulmonary embolism, bronchitis, obstructive pulmonary diseases, allergic pulmonary disease, infiltrative pulmonary disease, pneumonia, pulmonary tumor, cystic fibrosis, pleural diseases, lung cancer, etc.;

muscle diseases: spasmodic torticollis, fibromyalgia syndrome, bursitis, etc.;

splenic diseases: splenoma, etc.;

intestinal diseases: inflammatory intestinal disease, etc.;

liver diseases: fatty liver, cirrhosis, hepatitis, liver hematic diseases (veno-occlusive disease, Budd-Chiari syndrome, pylethrombosis, etc.), hematoma, cholecystolithiasis, choledocholithiasis, cholecystitis, cholangioma, etc.;

renal diseases: renal failure, nephritis, renal infarction, atherothrombotic renal diseases, cortical necrosis, malignant nephrosclerosis, renal vein thrombosis, etc.; and blood diseases: Ehlers-Danlos syndrome, Rendu-Osler-Weber syndrome, allergic purpura, thrombocytopenia, idiopathic thrombocytopenic purpura, thrombotic thrombocytopenic purpura, hemolytic uremic syndrome, platelet dysfunction, leukocyte diseases, leukemia, lymphoma, plasmocytic disorders, myeloproliferative diseases, etc.

The present invention also provides proteins functionally equivalent to the human, mouse or rat "BG37" protein. Such proteins can be prepared using methods known to those skilled in the art for modifying amino acids, for example, the Kunkel's method (Kunkel, T. A. et al., Methods Enzymol. 154, 367-382 (1987)); the double-primer method (Zoller, M. J. and Smith, M., Methods Enzymol. 154, 329-350 (1987)); the cassette mutagenesis (Wells, et al., Gene 34, 315-23 (1985)); and the mega-primer method (Sarkar, G. and Sommer, S. S., Biotechniques 8, 404-407 (1990)). Specifically, one skilled in the art can prepare modified proteins having equivalent function or activity to the human, mouse or rat natural "BG37" protein (SEQ ID NO: 2, 20 or 38) (e.g., the function to perform intracellular signaling via the activation of guanosine triphosphate-binding protein) by modification, such as substitution, of the amino acids in the natural protein according to known methods. Amino acid mutations may also occur in nature. The G protein-coupled receptor protein of the present invention also includes mutants functionally equivalent to the natural protein, which mutants have mutated amino acid sequences due to substitution, deletion, addition, or insertion of amino acids compared to the natural protein. The number of amino acid mutations in such a functionally equivalent protein is typically within 10% of the total number of amino acids, preferably 10 or less amino acids, more preferably 3 or less amino acids (for example, 1 amino acid); however there is no limitation on the number as long as the function of the protein is maintained.

A protein functionally equivalent to the human, mouse or rat "BG37" protein can also be prepared using hybridization techniques known to those skilled in the art (Hanahan, D. and Meselson, M., Meth. Enzymol. 100, 333-342 (1983); Benton, W. D. and Davis, R. W., Science 196, 180-182 (1977)). Specifically, one skilled in the art can carry out hybridization using human, mouse or rat "BG37" cDNA sequence (SEQ ID NO: 1, 19 or 37), or a portion thereof to isolate DNAs exhibiting high homology thereto from other various organisms, and then obtain a protein functionally equivalent to the "BG37" protein from the isolated DNAs. In the context of the present invention, a G protein-coupled receptor protein of the present invention also includes a protein functionally equivalent to the human, mouse or rat "BG37" protein, which is encoded by a DNA hybridizing to the human, mouse or rat "BG37" cDNA.

A stringent hybridization condition to isolate a DNA exhibiting high homology to human, mouse or rat "BG37" cDNA may be: hybridization in "6×SSC, 40% formamide at 25° C.", and washing in "1×SSC at 55° C.". A more preferable condition is: hybridization in "6×SSC, 40% formamide at 37° C.", and washing in "0.2×SSC at 55° C.". A further preferable condition is: hybridization in "6×SSC, 50% formamide at 37° C.", and washing in "0.1×SSC at 62° C.". One skilled in the art can achieve a stringent hybridization condition similar to the above-mentioned conditions by properly selecting various condition factors, such as dilution ratio of SSC, formamide concentration, and temperature.

Other organisms, from which a functionally equivalent protein can be isolated using the hybridization technique, include but are not limited to, for example, rabbit, bovine, dog, and monkey.

A DNA encoding a protein functionally equivalent to the human, mouse or rat "BG37" protein typically has a high homology to the nucleotide sequence of human, mouse or rat "BG37" cDNA (SEQ ID NO: 1, 19 or 37). The phrase "high homology" refers to sequence identity of at least 70% or higher, preferably 80% or higher, yet more preferably 90% or higher (for example, 95% or higher) at the nucleotide level. Amino acid sequence identity or nucleotide sequence identity can be determined based on the BLAST algorithm of Altschul et al. (J. Mol. Biol. 215, 403 410 (1990); Nucleic Acids Res. 17, 3389 3402 (1997)). For example, the parameters are set: E parameter value=0.01; and default values for the other parameters. Specific procedures of such analytical methods are well known in the art For example, see the web site of National Center for Biotechnology Information (NCBI), National Library of Medicine, Building 38A, Bethesda, Md. 20894, U.S.A.).

Likewise, a protein functionally equivalent to the human, mouse or rat "BG37" protein can be prepared using gene amplification techniques, such as polymerase chain reaction.

A protein of the present invention can be prepared not only as a natural protein but also as a recombinant protein, using gene recombination techniques. The natural protein can be prepared, for example, from an extract of heart tissue which is expected to express the human, mouse or rat "BG37" protein by conducting affinity chromatography using an "BG37" antibody described below. On the other hand, the recombinant protein can be prepared from cultured cells which have been transformed with a DNA encoding a protein of the present invention, as described below.

In addition, the present invention includes a partial peptide of the above-mentioned G protein-coupled receptor protein of the present invention. Such a partial peptide of the present invention includes, for example, a partial peptide of the N-terminal region of the G protein-coupled receptor protein of the present invention; and such partial peptides can be used to prepare antibodies. The peptide can also be used to screen for candidate compounds of pharmaceuticals, as described below. Such a partial polypeptide of the present invention is a polypeptide consisting of at least 10 amino acids, preferably 15 amino acids, more preferably 20 amino acids or more.

Furthermore, the present invention relates to a DNA encoding an above-mentioned G protein-coupled receptor protein of the present invention or a partial peptide thereof. There is no limitation on the type of DNA encoding a G protein-coupled receptor protein of the present invention or a partial peptide thereof, so long as it can encode such a protein or partial peptide, and includes cDNAs, genomic DNAs, and synthetic DNAs. Screening of a cDNA encoding a G protein-coupled receptor protein of the present invention can be carried out, for example, by hybridizing a cDNA of SEQ ID NO: 1, 19 or 37, fragments thereof, RNAs complementary thereto, or synthetic oligonucleotides containing a portion of the cDNA sequence, which has been labeled with $^{32}P$ or such, to a cDNA library derived from a tissue wherein a G protein-coupled receptor protein of the present invention is expressed. Alternatively, an oligonucleotide corresponding to the nucleotide sequence of the cDNAs can be synthesized, and then conduct amplification using a cDNA derived from an appropriate tissue as the template by polymerase chain reaction to clone a cDNA encoding a G protein-coupled receptor protein of the present invention. Genomic DNAs can be screened, for example, by hybridizing a genomic DNA library to the cDNA of SEQ ID NO: 1, 19 or 37, fragments thereof, RNAs complementary thereto, or synthetic oligonucleotides containing a portion of the cDNA sequence, which has been labeled with $^{32}P$ or such. Alternatively, an oligonucleotide corresponding to the nucleotide sequence of these cDNAs can be synthesized, and then conduct amplification using genomic DNA as the template by polymerase chain reaction to clone a genomic DNA encoding a G protein-coupled receptor protein of the present invention. On the other hand, a synthetic DNA can be prepared, for example, by chemically synthesizing oligonucleotides containing a partial sequence of the cDNA of SEQ ID NO: 1, 19 or 37, allowing them to anneal to a double-stranded DNA, and ligating them with DNA ligase (Khorana, H. G. et al., J. Biol. Chem. 251, 565-570 (1976); Goeddel, D. V. et al., Proc. Natl. Acad. Sci. USA 76, 106-110 (1979)).

These DNAs are useful for producing recombinant proteins. Specifically, a G protein-coupled receptor protein of the present invention can be prepared as a recombinant protein, by inserting a DNA encoding the particular G protein-coupled receptor protein of the present invention described above (for example, the DNA of SEQ ID NO: 1, 19 or 37) into a suitable expression vector; culturing a transformant obtained by introducing the resulting vector into a suitable cell; and purifying the expressed protein. The G protein-coupled receptor proteins of the present invention are receptor proteins, and thus can be expressed and prepared on the cell membrane.

Specifically, when the host is *E. coli* (*Escherichia coli*), plasmid vectors, such as pET-3 (Rosenberg, A. H. et al., Gene 56, 125-35 (1987)) and pGEX-1 (Smith, D. B. and Johnson, K. S., Gene 67, 31-40 (1988)), may be used. Transformation of *E. coli* can be achieved by the Hanahan's method (Hanahan, D., J. Mol. Biol. 166, 557-580 (1983)), electroporation (Dower, W. J. et al., Nucleic Acids Res. 16, 6127-6145 (1988)), and so on. When the host is a fission yeast, *Schizosaccharomyces pombe*, plasmid vector such as pESP-1 (Lu, Q. et al., Gene 200, 135-144 (1997)) can be used. Transformation of yeast can be carried out, for example, by the spheroplast method (Beach, D. and Nurse, P., Nature 290, 140 (1981)), the lithium acetate method (Okazaki, K. et al., Nucleic Acids Res. 18, 6485-6489 (1990)), etc.

On the other hand, when the host is a mammalian cell, such as CHO cell derived from Chinese hamster ovary, and human HeLa cell, vectors such as pMSG (Clontech) can be used. A recombinant DNA can be introduced into mammalian cells by the calcium phosphate method (Graham, F. L. and van derEb, A. J., Virology 52, 456-467 (1973)), the DEAE-dextran method (Sussman, D. J. and Milman, G., Mol. Cell. Biol. 4, 1641-1643 (1984)), the lipofection method (Feigner, P. L. et al., Proc. Natl. Acad. Sci. USA 84, 7413-7417 (1987)), electroporation (Neumann, E. et al., EMBO J. 1, 841-845 (1982)), etc. When the host is an insect cell, baculovirus vector pBacPAK8/9 (Clontech) or such can be used. Insect cell transformation can be achieved, for example, according to the method described in Bio/Technology 6, 47-55 (1980).

Recombinant proteins expressed in host cells can be purified by known methods. For example, when a recombinant protein is synthesized as a fusion protein containing a histidine tag or glutathione S-transferase (GST) at its N terminus, the protein can be purified by binding it to metal chelating resins or GST-affinity resins (Smith, M. C. et al., J. Biol. Chem. 263, 7211-7215 (1988)). For example, when pESP-1 is used as the vector, the protein of interest is synthesized as a fusion protein with glutathione S-transferase (GST), and thus the recombinant protein can be prepared by binding it to GST-affinity resins. Separation of the interest protein from the fusion protein can be achieved, for example, by digesting the fusion protein with thrombin, blood coagulation factor Xa, or the like.

A DNA encoding the G protein-coupled receptor protein of the present invention can be used in gene therapy for diseases caused by a mutation in the DNA. Introduction of a gene into human cells for gene therapy can be achieved by methods using retroviral vectors (Danos, O. and Mulligan, R. C., Proc. Natl. Acad. Sci. USA 85, 6460-6464 (1988); Dranoff, et al., Proc. Natl. Acad. Sci. USA 90, 3539-3543 (1993)), adenoviral vectors (Wickham, T. J. et al., Cell 73, 309-319 (1993)), and such. Administration into a patient can be performed by bone marrow transplantation, subcutaneous injection, intravenous injection, and so on (Asano, S., Protein Nucleic Acid, and Enzyme, 40, 2491-2495 (1995)).

The present invention also relates to antibodies which bind to a G protein-coupled receptor protein of the present invention. Antibodies binding to a G protein-coupled receptor protein of the present invention can be prepared by methods known to those skilled in the art (for example, see "Shinseika-gakujikken Kouza 1, Tanpakushitsu I (New series of Lecture for Biochemical Experiment 1, Protein I), 389-406, TOKYO KAGAKU DOZIN CO.). Polyclonal antibodies can be prepared, for example, as follows: an appropriate amount of the above-mentioned protein or peptide is administered to an animal to be immunized, such as rabbit, guinea pig, mouse, and chicken. An adjuvant (FIA or FCA), which enhances antibody production, can be administered together with the protein or peptide. Typically, the administration is conducted every several weeks. The antibody titer can be raised by immunizing several times. After final immunization, antiserum can be obtained by collecting blood from the immunized animal. Polyclonal antibodies can be prepared from the antiserum, for example, by fractionation with ammonium sulfate precipitation or anion-exchange chromatography, or affinity purification using protein A or immobilized antigen.

On the other hand, monoclonal antibodies can be prepared, for example, as follows: the G protein-coupled receptor protein of the present invention or a partial peptide thereof is immunized to an animal similarly as described above, and after the final immunization, spleen or lymph node is collected from the immunized animal. Hybridomas are prepared by fusing myeloma cells with antibody-producing cells comprised in the spleen or lymph node using polyethylene glycol or such. The hybridomas of interest are screened and cultured to prepare monoclonal antibodies from the culture supernatant. The monoclonal antibodies can be purified, for example, by fractionation with ammonium sulfate precipitation or anion-exchange chromatography, or affinity purification using protein A or immobilized antigen. The resulting purified antibodies can be used in tests and antibody therapy for a disease caused by aberrant expression of the G protein-coupled receptor protein of the present invention, and in detecting the expression level of the G protein-coupled receptor protein of the present invention, as well as in affinity purification of the G protein-coupled receptor protein of the present invention.

To use the antibodies in antibody therapy, preferably the antibody is a humanized antibody or human antibody. A humanized antibody, for example, a mouse-human chimera antibody, can be prepared by isolating the antibody gene from a mouse cell producing an antibody against a G protein-coupled receptor protein of the present invention, recombining its H chain constant region with the human IgE H chain constant region gene, and introducing the recombined gene into mouse myeloma cell J558L (Neuberger, M. S. et al., Nature 314, 268-270 (1985)). A human antibody, on the other hand, can be prepared by immunizing a mouse with a G protein-coupled receptor protein of the present invention, wherein the immune system of the mouse has been replaced with that of human.

The present invention also relates to a method of screening for a ligand of a G protein-coupled receptor protein of the present invention or an analog of the ligand. This screening method comprises the steps of contacting a test compound with a G protein-coupled receptor protein of the present invention or a partial peptide thereof, and selecting the compound that binds to the protein or peptide. The test compounds include, for example: known compounds such as acetylcholine, adenosine, adrenalin, noradrenaline, angiotensin, bombesin, bradykinin, C5a anaphylatoxin, calcitonin, cannabinoid, chemokine, cholecystokinin, dopamine, endothelin, formylmethionine peptide, GABA, galanin, glucagon, glutamic acid, glycopeptide hormone, histamine, 5-hydroxytryptophan, leukotriene, melanocortin, neuropeptide Y, neurotensin, odorant, opioid peptide, opsin, parathyroid hormone, platelet-activating factor, prostanoid, somatostatin, tachykinin, thrombin, thyrotropin-releasing hormone, vasopressin, oxytocin (Watson, S. and Arkinstall, S., The G-Protein Linked Receptor FactsBook, Academic Press (1994)), and analogs thereof; other purified proteins; expression products of genes (including libraries); extract of tissues or cells expected to contain a ligand; and cell culture supernatant. The G protein-coupled receptor protein of the present invention used in the screening may be, for example, in a form expressed in or on the surface of a desired cell (including a transformant which has been treated to express the protein), in a form of membrane fraction of the cell, or in a form where the protein is bound to an affinity column. The test compound used in the screening may be appropriately labeled if required. Such labels include, but are not limited to, radiolabels and fluorescent labels. The binding of a G protein-coupled receptor protein of the present invention with a test compound can be detected due to a label attached to the compound, which is bound to the G protein-coupled receptor protein of the present invention (for example, the amount of bound protein is determined by the radioactivity or fluorescence intensity). Alternatively, the binding can be detected using, as an indicator, an intracellular signal transduction (for example, activation of G protein, changes in the $Ca^{2+}$ or cAMP concentration, activation of phospholipase C, or pH change) induced by the binding of the test compound to the G protein-coupled receptor protein of the present invention on the cell surface. Specific methods are described, for example, in the following references: Cell Calcium 14, 663-671 (1993); Analytical Biochemistry 226, 349-354 (1995); J. Biol. Chem. 268, 5957-5964 (1993); Cell 92, 573-585 (1998); Nature 393, 272-273 (1998)); and patent publication: Unexamined Published Japanese Patent Application No. (JP-A) Hei 9-268. In addition, the binding can be detected by detecting the reporter gene activity using TWO HYBRID SYSTEM (Zervos et al., Cell 72, 223-232 (1994); Fritz et al., Nature 376, 530-533 (1995)).

The present invention also relates to a method of screening for compounds having the activity to inhibit the binding between a G protein-coupled receptor protein of the present invention and a ligand thereof or analog of the ligand. The screening method comprises the steps of: (a) contacting a ligand or an analog thereof with a G protein-coupled receptor protein of the present invention or a partial peptide thereof in the presence of a test compound, and detecting the binding activity of the protein or partial peptide thereof with the ligand or analog thereof; and (b) comparing the binding activity detected in step (a) with that in the absence of the test compound, and selecting the compound which decreases the binding activity of the G protein-coupled receptor protein of the present invention or partial peptide thereof with the ligand or analog thereof.

The test compounds include, but are not limited to, proteins, peptides, non-peptidic compounds, artificially synthesized compounds, cell or tissue extracts, and serum. The G protein-coupled receptor protein of the present invention used in the screening may be, for example, in a form expressed in or on the surface of a desired cell (including a transformant which has been tested to express the protein), in a form of membrane fraction of the cell, or in a form where the protein is bound to an affinity column. The ligand to be used in the screening may be previously labeled appropriately if required. The labels include, but are not limited to, radiolabels and fluorescent labels.

The binding activity of the present invention G protein-coupled receptor protein or a partial peptide thereof with a ligand or an analog thereof can be detected using a label attached to the ligand or analog thereof, which is bound to the present invention G protein-coupled receptor protein or a partial peptide thereof (for example, the amount of bound protein is determined by the radioactivity or fluorescence intensity), or alternatively using, as an indicator, changes in the cell resulting from the binding of a test compound to the G protein-coupled receptor protein of the present invention on the cell surface (for example, activation of G protein, changes in the $Ca^{2+}$ or cAMP concentration, activation of phospholipase C, and pH change). Specifically, for example, the method of Zlokarmik et al. (Science 279, 84 (1998)) described in Examples below may be used. Alternatively, other methods of the prior art such described in the following can be used: Cell Calcium 14, 663-671 (1993); Analytical Biochemistry 226, 349-354 (1995); J. Biol. Chem. 268, 5957-5964 (1993); Cell 92, 573-585 (1998); Nature 393, 272-273 (1998)); or the patent publication: JP-A No. Hei 9-268. When the binding activity in the presence of the test compound is lower than that in the absence of the compound (control) according to the detection, the test compound is determined to have the activity to inhibit the binding of the G protein-coupled receptor protein of the present invention or a partial peptide thereof with a ligand or an analog thereof. Such compounds include compounds which bind to a G protein-coupled receptor protein of the present invention and either have the activity to induce intracellular signaling (agonist) or lack such inducing activity (antagonist). An agonist has a biological activity similar to that of a ligand of the G protein-coupled receptor protein of the present invention. On the other hand, the antagonist suppresses the physiological activity of a ligand of the G protein-coupled receptor protein of the present invention. Thus, the agonists and antagonists are useful as pharmaceutical compositions for treating diseases caused by abnormalities in the signaling system via the G protein-coupled receptor protein of the present invention.

Furthermore, the present invention relates to a method of screening for compounds which inhibit or enhance the activity of a G protein-coupled receptor protein of the present invention. The screening method comprises the steps of: (a) contacting a cell expressing a G protein-coupled receptor protein of the present invention with a ligand of the protein or an analog of the ligand in the presence of a test compound; (b) detecting the alteration in the cell due to the binding of the protein with the ligand or analog thereof; and (c) comparing the alternation in the cell with that in the absence of the test compound, and selecting the compound that suppresses or enhances the alteration detected in step (b).

Such test compounds include, but are not limited to, proteins, peptides, non-peptidic compounds, artificially synthesized compounds, cell or tissue extracts, and serum. The above-mentioned compounds isolated by the screening utilizing the inhibition of the binding activity as an indicator may be also used as the test compound. A cell which expresses a G protein-coupled receptor protein of the present invention can be prepared, for example, by inserting a DNA encoding the protein into an appropriate expression vector, and introducing the resulting vector into an appropriate animal cell. The expression vector may contain a marker gene to select transformants.

An alteration in a cell resulting from the binding of a ligand or analog thereof to a G protein-coupled receptor protein of the present invention can be detected, for example, using the activation of G protein, changes of $Ca^{2+}$ or cAMP concentration, activation of phospholipase C, and pH change as an indicator. Specific methods which can be used for the present invention include, for example, the method of Zlokarmik et al. (Science 279, 84 (1998)). Alternatively, other methods of the prior art, such as those described in the following can also be used: Cell Calcium 14, 663-671 (1993); Analytical Biochemistry 226, 349-354 (1995); J. Biol. Chem. 268, 5957-5964 (1993); Cell 92, 573-585 (1998); Nature 393, 272-273 (1998); or the patent publication (JP-A Hei 9-268).

As a result of the detection, when the alteration in the cell is suppressed as compared to that in a cell which was contacted with the ligand or analog in the absence of the test compound, the used test compound is judged to inhibit the activity of the G protein-coupled receptor protein of the present invention. Conversely, when the test compound enhances the alteration in the cell, the compound is determined to enhance the activity of the G protein-coupled receptor protein of the present invention.

Compounds (agonists and antagonists of the protein of the present invention) isolated by the screening method of the present invention can be used to treat rheumatic arthritis, osteoarthritis, gastric ulcer, inflammatory intestinal diseases, ischemic heart disease, cardiac arrhythmia, hypertension, hypotension, obesity, asthma, pain, allergic diseases, autoimmune disease (Trends in Pharmacological Science 19, 177-183 (1998); Stark, H. et al., Drugs of the Future 21, 507-520 (1996); Onodera, K. and Watanabe, T., Jpn. J. Psychopharmacol. 15, 87-102 (1995)). When these compounds are used as a pharmaceutical, isolated compounds may be administered as a pharmaceutical composition formulated by known pharmaceutical methods, in addition to direct administration to a patient. For example, such compounds can be appropriately formulated and administered in combination with pharmaceutically acceptable carriers or solvents; specifically such as sterile water, physiological saline, vegetable oils, emulsifiers, suspensions, detergents, stabilizers, binders, lubricants, sweeteners, flavoring agents, and colorants. The compounds can be administered to a patient by methods known to those skilled in the art, such as intranasal, transbronchial, intramuscular, or oral administrations as well as intraarterial injection, intravenous injection, or subcutaneous injection. The dose depends on patient's weight and age, and the method of administration. However, one skilled in the art can routinely select an appropriate dose.

Furthermore, the present invention relates to a kit for the above-described screening of the present invention, which comprises a G protein-coupled receptor protein of the present invention or a partial peptide thereof. The G protein-coupled receptor protein of the present invention or a partial peptide thereof in the kit of the present invention can be, for example, in a form expressed in or on the surface of a desired cell (including a transformant which has been treated to express the protein), in a form of membrane fraction of the cell, or in a form where the protein is bound to an affinity column. The kit of the present invention may contain, in addition to the above-mentioned receptor protein sample, for example, ligand samples (labeled and non-labeled), buffer for the reaction between the ligand and receptor protein, and washing solution. Such labels to be attached to the ligand include, for example, radiolabels and fluorescent labels. The kit of the present invention can be used according to the patent publication JP-A Hei 9-268. For example, the kit of the present invention can be used in a screening which utilizes a system to detect the changes in cAMP level or binding activity.

BEST MODE FOR CARRYING OUT THE INVENTION

Figure 1:
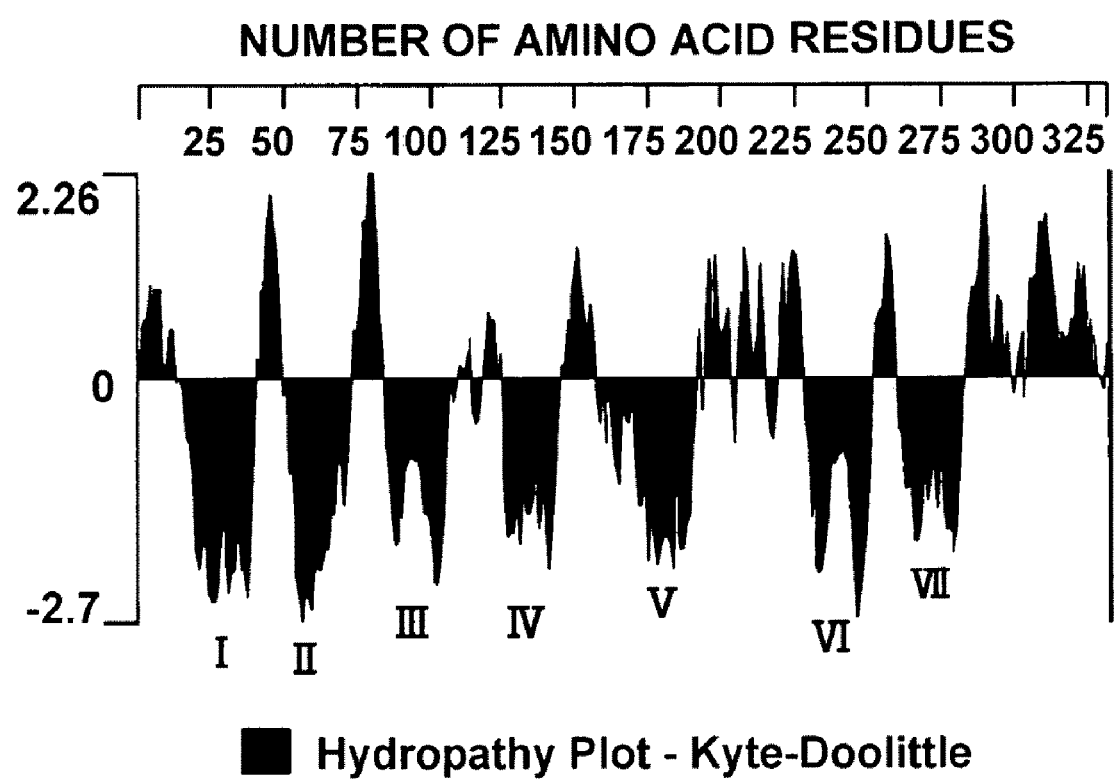
FIG. 1 is a diagram showing the hydropathy plot of the "BG37" protein. The numbers above the diagram correspond to the amino acid numbers in the human "BG37" protein. The seven hydrophobic domains are marked with numbers I to VII.

The present invention is illustrated in detail below with reference to Examples, but is not to be construed as being limited thereto.

Example 1

Search for Novel Candidate Genes for GPCR

A similarity search of approximately 400 known GPCR amino acid sequences was carried out in the GenBank high throughput genomic division. Blast was used as the search algorithm. A list was made of the identified sequences which exhibited similarity to the known GPCR sequences. Then, these nucleotide sequences were searched for similarity in known GPCR database to confirm whether the nucleotide sequences are identical to a known GPCR and, when not identical, to determine the degree of similarity. As a result, candidate sequences for novel GPCRs were identified. AC021016 was identified as one of such candidates. This novel candidate GPCR gene was dubbed human "BG37".

Example 2

Cloning of human BG37 cDNA

Two primers, BG37-01F (5'-CTACATGGCAGTCCT-GAGGC-3'/SEQ ID NO: 3) and BG37-02R (5'-ACT-GAGAGGAGCAGTGTGGC-3'/SEQ ID NO: 4), were synthesized to amplify a 414-bp fragment of AC021016 which was confirmed to exhibit similarity to the nucleotide sequences of known GPCRs. Using these primers, the fragment of interest was amplified from human genome gene (CLONTECH) by PCR. The PCR was carried out according to the protocol of AmpliTaq Gold from Perkin Elmer: i.e., heating at 95° C. for 9 minutes; 39 cycles of 94° C. for 30 seconds, 55° C. for 15 seconds, and 72° C. for 1 minute; and finally heating at 94° C. for 30 seconds and at 62° C. for 10 minutes. Then, the amplified product was subcloned into plasmid vector pCR2.1-TOPO (Invitrogen). Dideoxy sequencing reaction was carried out using Dye Primer Cycle Sequencing Kit FS (PE Applied Biosystems). The sample was electrophoresed on DNA sequencer 377 (PE Applied Biosystems) to determine the nucleotide sequences.

The genetic information on the C-terminus of the human BG37 fragment was gained by 3'-Rapid amplification of cDNA Ends (3'-RACE) according to the method of Clontech. Primer BG37-10F (5'-CGTGGCCACACTGCTCCTCT-CAGTC-3'/SEQ ID NO: 5) was synthesized, and then a fragment of about 500 by was amplified from Marathon-Ready fetus cDNA (Clontech) by PCR using the primer. The PCR was carried out using AmpliTaq Gold from Perkin Elmer by heating at 94° C. for 9 minutes, 35 cycles of 94° C. for 30 seconds and 68° C. for 3 minutes, and finally heating at 94° C. for 30 seconds and at 62° C. for 8 minutes. Then, the amplified product was subcloned into plasmid vector pCR2.1-TOPO (Invitrogen). Dideoxy sequencing reaction was carried out using Dye Primer Cycle Sequencing Kit FS (PE Applied Biosystems). The sample was electrophoresed on DNA sequencer 377 (PE Applied Biosystems) to determine the nucleotide sequences.

The nucleotide sequence newly identified by 3'-RACE was assembled with the sequence of human BG37 fragment obtained above. The resulting sequence was subjected to similarity search in GenBank high throughput genomic division. The algorithm used in the search was blast. As a result, AC055884 was found to share the same nucleotide sequence as identified above. The nucleotide sequences of AC05584 and AC021016 were found to be identical, except for a single-nucleotide gap in AC021016. Based on the nucleotide sequence information of AC055884 and AC021016, the start codon of human BG37 was found, and the open reading frame (ORF) of the human BG37 was predicted to be 993 by in length.

Primers BG37-12F (5'-CCCCTGTCCCCAGGACCAA-GATG-3'/SEQ ID NO: 6) and BG37-15R (5'-TTAGT-TCAAGTCCAGGTCGACACTGCTTT-3'/SEQ ID NO: 7) were synthesized to clone a cDNA containing the ORF of human BG37. The fragment of interest was amplified by PCR from human genomic gene (CLONTECH) using the primers BG37-12F and BG37-15R. The PCR was carried out using AmpliTaq Gold from Perkin Elmer by heating at 94° C. for 9 minutes, 26 cycles of 94° C. for 30 seconds and 68° C. for 3 minutes, and finally heating at 94° C. for 30 seconds and at 62° C. for 8 minutes. Then, the amplified product was subcloned into plasmid vector pCR2.1-TOPO (Invitrogen) (pCR2.1-BG37ORF). Dideoxy sequencing reaction was carried out using Dye Primer Cycle Sequencing Kit FS (PE Applied Biosystems). The sample was electrophoresed on DNA sequencer 377 (PE Applied Biosystems) to determine the nucleotide sequences. The amino acid sequence was deduced using LASERGENE (DNA STAR).

The deduced amino acid sequence of the protein was found to consist of 330 residues and the protein was predicted to be a seven-transmembrane receptor.

*E. coli* strain containing the BG37 cDNA clone (*E. coli* hBG37-2) was deposited as follows:

(1) Name and Address of Depositary Institution

Name: International Patent Organism Depositary, National Institute of Advanced Industrial Science and Technology (AIST), Independent Administrative Institution (Previous Name: The National Institute of Bioscience and Human-Technology, The Agency of Industrial Science and Technology, The Ministry of International Trade and Industry)

Address: AIST Tsukuba Central 6, 1-1-1 Higashi, Tsukuba, Ibaraki, Japan (Zip code: 305-8566)

(2) Date of Deposition (Date of Initial Deposition): Nov. 2, 2000

(3) Accession Number: FERM BP-7739

Example 3

Expression Analysis of Human BG37

Northern hybridization for human BG37 was carried out using Multiple Tissue Northern Blot (human 12-lane MTN Blot, Clontech). The fragment amplified by PCR with the primers BG37-12F and BG37-15R using pCR2.1-BG37ORF as the template, i.e., the ORF portion of human BG37, was purified using PCR purification kit (Qiagen); and then used as a probe for Northern hybridization. The PCR was carried out using AmpliTaq Gold from Perkin Elmer by heating at 94° C. for 9 minutes, 26 cycles of 94° C. for 30 seconds and 68° C. for 3 minutes, and finally heating at 94° C. for 30 seconds and at 62° C. for 8 minutes. The probe was labeled with [α-$^{32}$P] dCTP using BcaBEST Labeling kit (TAKARA). Rapid Hyb Buffer (Amersham Pharmacia Biotech) was used as the hybridization buffer. Following the pre-hybridization of MTN Blot in Rapid Hyb Buffer for 1 hour, the labeled probe was added thereto. Then, hybridization was carried out for 2 hours. To remove the nonspecifically hybridized probes, the blot was washed twice with 2×SSC/0.1% SDS at room temperature, and then twice with 0.1×SSC/0.1% SDS at 65° C. for 20 minutes. The blot was then exposed on an imaging plate (Fuji Film) overnight and analyzed on BAS2000 (Fuji Film).

Figure 2:
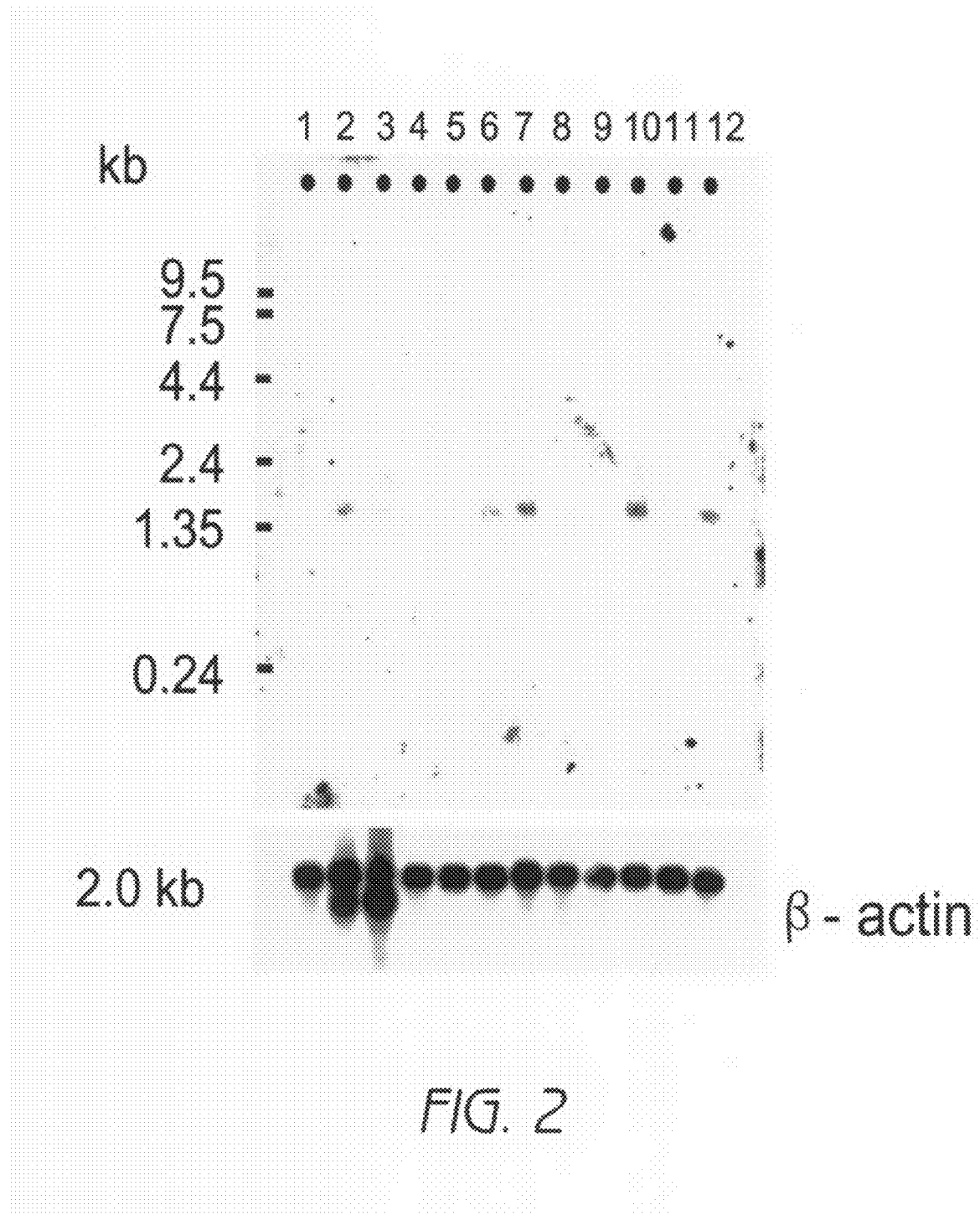
FIG. 2 depicts photographs. The upper photograph shows the result of detecting human "BG37" expression in various tissues by Northern blot hybridization. The lower photograph shows the result of detecting β actin expression in various tissues by Northern blot hybridization. Lanes 1 to 12 in the figure correspond to brain, heart, skeletal muscle, large intestine (without mucus membrane), thymus, spleen, kidney, liver, small intestine, placenta, lung, and peripheral blood leukocyte, respectively.

The results of Northern hybridization are shown in FIG. 2. Human BG37 mRNA was expressed in the heart, skeletal muscle, spleen, kidney, liver, small intestine, placenta, lung, peripheral blood leukocyte with a length of approximately 1.5 kb. No detection could be confirmed in the brain, colon, and thymus.

Example 4

Preparation of Human BG37-Expressing Cells (Human BG37-Stable Cell Line)

A human BG37 expression vector was prepared using pIRESneo and pIREShyg (CLONTECH). For the convenience of cloning the human BG37 gene, a plasmid (pKT52) wherein the neomycin resistance gene of pIRESneo had been replaced with the hygromycin resistance gene of pIREShyg, was prepared. Human BG37 gene cut out, utilizing the BamHI-EcoRV site, from pCR2.1-BG37ORF was subcloned into the BamHI-EcoRV digested pKT52 vector to construct an expression vector (pKT52-hBG37-2).

HEK293 cells were cultured at 37° C. under 5% $CO_2$ in D-MEM/F-12 (1:1) mixed culture medium (Asahi Technoglass Corporation) containing 10% bovine fetal serum and neomycin.

Gene introduction was performed using Lipofectamine plus Reagent (GIBCO BRL). On the day before transfection, $1\times10^6$ cells were plated on a 6-cm dish (coated with type I collagen) (Asahi Technoglass Corporation). 2 µg pKT52-hBG37-2 was transfected into the cells using 12 µl of Lipofectamine Reagent and 8 µl of plus Reagent according to the provided manual, and then the cells were incubated at 37° C. under 5% $CO_2$ for 48 hours.

In order to isolate single-cell clones introduced with the gene of interest, the transfected cells were treated with trypsin, and then harvested by centrifugation. The cells were re-suspended in D-MEM/F-12 (1:1) mixed culture medium (Asahi Technoglass Corporation) and further cultured in selection medium containing hygromycin at 37° C. under 5% $CO_2$ for 11 days. Single-colony cells were selected and passaged to prepare stable cell lines.

Total RNA was extracted from human BG37-expressing cells prepared as described above. The expression level of the introduced human BG37 was determined by Northern hybridization. Cells (HEK/hBG37) expressing the gene at a high level were selected and used in subsequent experiments.

Example 5

Assay of Intracellular cAMP Level (ELISA)

Intracellular cAMP levels were determined using the method of Zlokarmik et al. (Science 279, 84 (1998)). The intracellular cAMP level in cells that reacted with the ligand was measured to determine the increase of intracellular cAMP level through G proteins bound to the seven-transmembrane receptor.

On the day before the measurement of the intracellular cAMP level, cells were re-plated at a cell density of $4\times10^4$ cells/well on a poly-D-lysin-coated 96-well plate (Becton Dickinson), and then incubated at 37° C. for another 24 hours. Cells of the stable cell line were rinsed twice with 0.1% BSA (SIGMA) and 1 mM 3-Isobutyl-1-Methylxanthine containing Opti-MEM solution (GIBCO BRL: Opti-MEM-BSA-IBMX solution) (Nacalai Tesque Inc.: IBMX), and then incubated at 37° C. for 20 minutes. After removing the supernatant, Opti-MEM-BSA-IBMX solution containing at various concentrations a steroid hormone, such as progesterone, was added thereto. The resulting mixture was incubated at 37° C. for 15 minutes. Then, the cells were lysed with Lysis Buffer to measure the level of intracellular cAMP.

The measurement of the intracellular cAMP level was carried out using cyclic AMP enzyme immuno-assay (EIA) system (Amersham Pharmacia Biotech) according to the provided manual.

Figure 3:
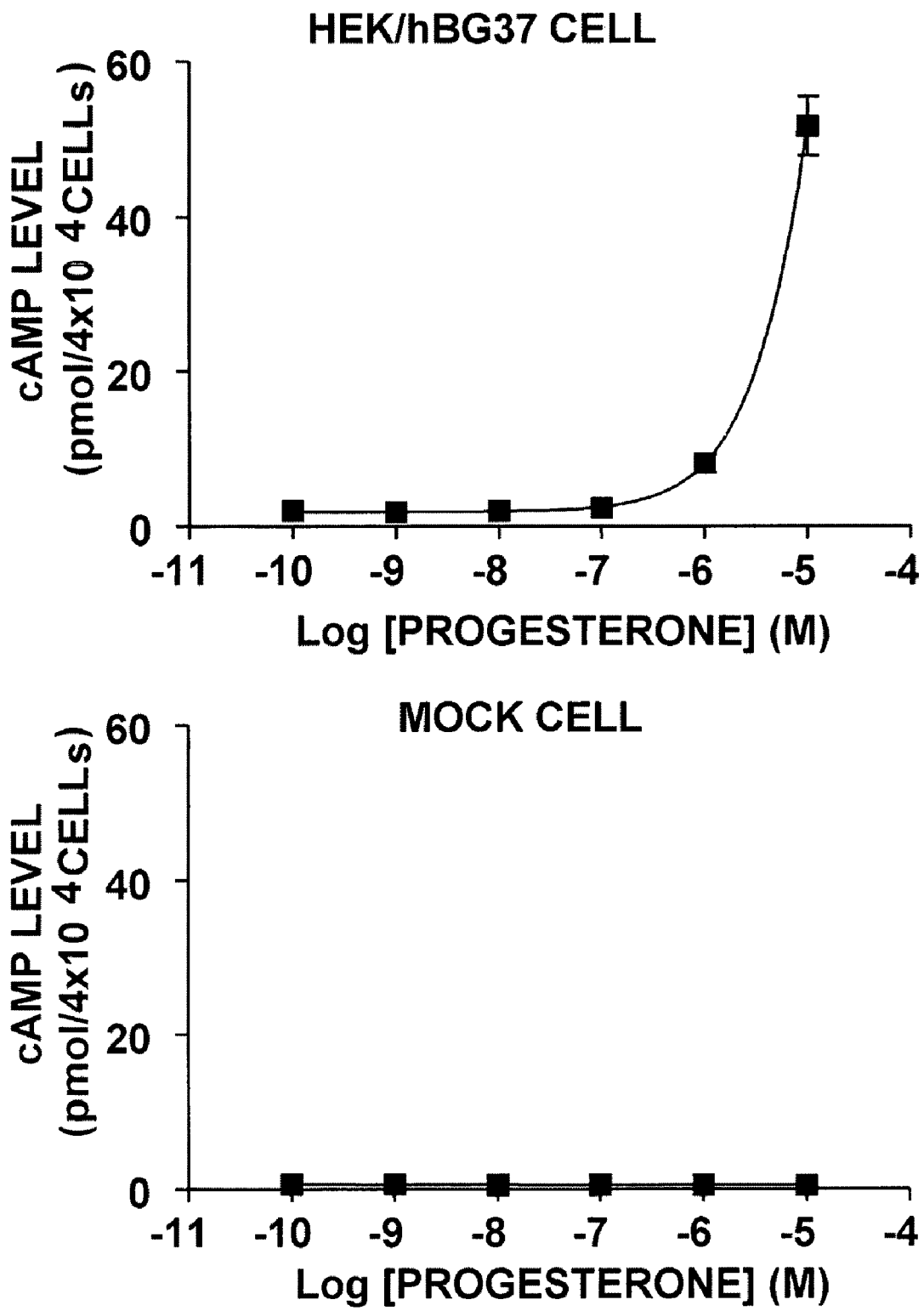
FIG. 3 depicts graphs showing the result of the increase in the intracellular cAMP level upon the addition of progesterone. The upper panel corresponds to the result obtained with HEK/hBG37 cells; the lower panel with mock-transfected cells which express the vector alone (control cells). The horizontal axis indicates the progesterone concentration (M) in logarithmic scale; and the longitudinal axis the cAMP level.

As a result, in cells expressing the human BG37 (HEK/hBG37), the intracellular cAMP level increased in a concentration-dependent manner in the presence of steroid hormones including progesterone, dehydroisoandrosterone, testosterone, androstenedione, and pregnenolone. A representative data is shown, which exhibits an increase of the intracellular cAMP in progesterone concentration-dependent manner. On the other hand, such progesterone concentration-dependent increase of intracellular cAMP was not observed for mock-transfected cells which contained the vector alone (FIG. 3).

Thus, steroid hormones, at least such as progesterone, dehydroisoandrosterone, testosterone, androstenedione, and pregnenolone, were revealed to specifically increase the intracellular cAMP level via the BG37.

Example 6

Cloning of Mouse BG37 cDNA

In order to clone a cDNA of mouse BG37, a fragment of approximately 490 by was amplified by PCR using mouse genomic gene (CLONTECH) as a template with two primers, BG37-13F (5'-CTGCCTCCTCGTCTACTTGGCTCC-3'/SEQ ID NO: 8) and BG37-14R (5'-TGAGAGGAGCAGT-GTGGCCACGTAGGGC-3'/SEQ ID NO: 9), which had been designed based on the sequence of human BG37. The PCR was carried out according to the protocol of AmpliTaq Gold from Perkin Elmer by heating at 95° C. for 9 minutes; 30 cycles of 94° C. for 30 seconds, 52° C. for 30 seconds, and 72° C. for 1 minute; and finally heating at 94° C. for 30 seconds and at 62° C. for 10 minutes. Then, the amplified product was subcloned into plasmid vector pCR2.1-TOPO (Invitrogen), and the nucleotide sequence was determined (SEQ ID NO: 10). The result of the homology search between the sequence of mouse BG37 fragment and that of human BG37, showed that they share 84.4% homology. This strongly suggests that the obtained nucleotide sequence is the sequence of mouse BG37 of interest. Dideoxy sequencing reaction was carried out using Dye Primer Cycle Sequencing Kit FS (PE Biosystems). The sample was electrophoresed on DNA sequencer 377 (PE Biosystems) to determine the nucleotide sequences.

The genetic information on the C-terminus of the mouse BG37 fragment was obtained by 3'-RACE and nested PCR according to the method of Clontech. Primer mBG37-04F (5'-CCCTCAACCCTGGCTAGGGCTCTCACC-3'/SEQ ID NO: 11) was used in the 3'-RACE, and PCR was carried out using Marathon-Ready mouse heart cDNA (Clontech). Then, the nested-PCR was carried out using the resulting PCR product as a template with primer mBG37-03F (5'-GCCACACT-GCTCTTCTTGCTGTGTTGGGG-3'/SEQ ID NO: 12). The obtained PCR product was subcloned into plasmid vector pCR2.1-TOPO (Invitrogen) to determine the nucleotide sequence (SEQ ID NO: 13).

Similarly, 5'-RACE and nested-PCR were carried out according to the method of Clontech to obtain the genetic information on the N-terminus of the fragment of the mouse BG37. The 5'-RACE was performed by PCR using primer mBG37-09R (5'-GCTGACCCAGGTGAGGAA-CAGGGCTAGCCGC-3'/SEQ ID NO: 14) and Marathon-Ready mouse heart cDNA (Clontech). Then, nested-PCR was carried out using the resulting PCR product as a template with mBG37-07R (5'-GCAGATTGGCAAGCAGGGAAAG-GAAACAAAAG-3'/SEQ ID NO: 15). The obtained FOR product was subcloned into plasmid vector pCR21-TOPO (Invitrogen) to determine the nucleotide sequence (SEQ ID NO: 16).

Primers mBG37-12F (5'-GTGCCAAGACCCATGATGA-CACCC-3'/SEQ ID NO: 17) and mBG37-13R (5'-CTAAT-TCAAGTCCAGGTCAATGCTGC-3'/SEQ ID NO: 18) were synthesized to clone a cDNA containing the ORF of mouse BG37. The fragment of interest was amplified from Marathon-Ready mouse heart cDNA (CLONTECH) by PCR using mBG37-12F and mBG37-13R. The PCR was carried out using AmpliTaq Gold from Perkin Elmer by heating at 94° C. for 9 minutes; 35 cycles of 94° C. for 30 seconds, 58° C. for 30 seconds, and 72° C. for 2 minutes; and finally heating at 94° C. for 30 seconds and at 62° C. for 10 minutes. Then, the PCR product was subcloned into plasmid vector pCR2.1-TOPO (Invitrogen) (pCR2.1-mBG37-9) to determine the nucleotide sequence of mouse BG37 ORF (SEQ ID NO: 19).

The ORF was predicted to be 990 by in length and was deduced to encode a protein of 329 amino acids. The degree of homology of the mouse BG37 to human BG37 was found to be 83% at the DNA level and 84% at the amino acid level.

The *E. coli* strain containing the mouse BG37 cDNA clone (*E. coli* mBG37-9) was deposited as follows:

(1) Name and Address of Depositary Institution

Name: International Patent Organism Depositary, National Institute of Advanced Industrial Science and Technology (AIST), Independent Administrative Institution (Previous Name: The National Institute of Bioscience and Human-Technology, The Agency of Industrial Science and Technology, The Ministry of International Trade and Industry)

Address: AIST Tsukuba Central 6, 1-1-1 Higashi, Tsukuba, Ibaraki, Japan (Zip code: 305-8566)

(2) Date of Deposition (Date of Initial Deposition): Feb. 1, 2001

(3) Accession Number: FERM BP-7740

Example 7

Expression Analysis of Mouse BG37

Figure 4:
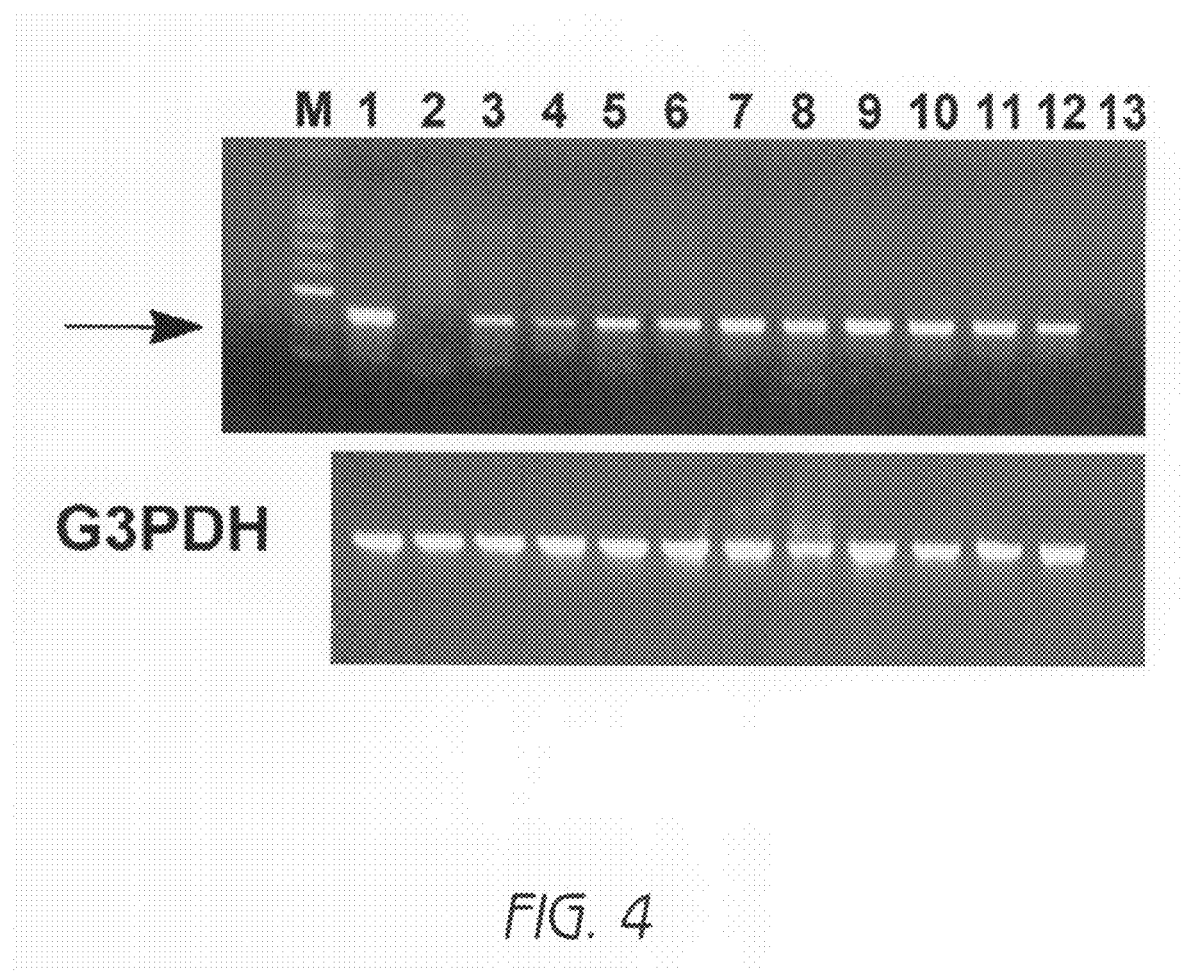
FIG. 4 depicts photographs. The upper photograph shows the result of examining the mouse "BG37" expression site using mouse MTC panel I. The lower photograph shows the result of detecting G3PDH expression in various tissues. Lanes 1 to 13 correspond to heart, brain, spleen, lung, liver, skeletal muscle, kidney, testis, embryos of day-7, -11, -15, and -17, and negative control (no template), respectively. Lane M corresponds to the size marker.

PCR was carried out using Multiple Tissue cDNA panel (mouse MTC panel I, Clontech) to identify the expression sites of mouse BG37. mBG37-1F (5'-TTCCCTGCTTGC-CAATCTGCTGCTGG-3'/SEQ ID NO: 21) and mBG37-2R (5'-CACAGCAAGAAGAGCAGTGTGGCTCC-3'/SEQ ID NO: 22) were used as primers. The PCR was carried out using AmpliTaq Gold from Perkin Elmer by heating at 94° C. for 9 minutes; 40 cycles of 94° C. for 30 seconds, 55° C. for 30 seconds, and 72° C. for 2 minutes; and finally heating at 94° C. for 30 seconds and at 62° C. for 10 minutes. The results of electrophoresis of the PCR product on agarose gel are shown in FIG. 4. The size of the PCR product was about 420 bp. The mouse BG37 was found to be expressed in the heart, spleen, lung, liver, skeletal muscle, kidney, testis, and embryos of day-7, -11, -15, and day-17. No expression was detected in the brain.

Example 8

Cloning of Rat BG37 cDNA

In order to clone a cDNA of rat BG37, a fragment of approximately 490 by was amplified by PCR using rat genomic gene (CLONTECH) as a template with the two primers, BG37-13F and BG37-14R, which were designed based on the sequence of human BG37. The PCR was carried out according to the protocol of AmpliTaq Gold from Perkin Elmer by heating at 95° C. for 9 minutes; 30 cycles of 94° C. for 30 seconds, 52° C. for 30 seconds, and 72° C. for 1 minute; and finally heating at 94° C. for 30 seconds and at 62° C. for 10 minutes. Then, the amplified product was subcloned into plasmid vector pCR2.1-TOPO (Invitrogen), and the nucleotide sequence was determined (SEQ ID NO: 23). The result of homology search between the sequence of rat BG37 fragment to that of human BG37 showed that they shared 84.2% homology. This strongly suggested that the obtained nucleotide sequence is the sequence of rat BG37 of interest. Dideoxy sequencing reaction was carried out using Dye Primer Cycle Sequencing Kit FS (PE Biosystems). The sample was electrophoresed on DNA sequencer 377 (PE Biosystems) to determine the nucleotide sequences.

Using the full length sequence of human BG37 cDNA as a query, GenBank was searched for sequences with similarity based on the blast algorithm. A rat EST clone (AI548141) was revealed to encode the C-terminus of the rat BG37. Primer rBG37-12R (5'-CCCTAATTCAAGTCCAAGTCAGTG-3'/SEQ ID NO: 24) was prepared based on the sequence of AI548141; and primer rBG37-3F (5'-GCCACACT-GCTCTTTTTGCTGTGTTGGGG-3'/SEQ ID NO: 25) was prepared based on the sequence of the rat BG37 fragment obtained above. PCR was carried out using rat genomic gene and rat marathon ready kidney cDNA (both from CLONTECH) as templates. Reactions with both templates gave an amplified fragment of 311-bp. The PCR was carried out according to the protocol of AmpliTaq Gold from Perkin Elmer by heating at 95° C. for 9 minutes; 40 cycles of 94° C. for 30 seconds, 58° C. for 30 seconds, and 72° C. for 1 minute; and finally heating at 94° C. for 30 seconds and at 62° C. for 10 minutes. Then, the amplified products were subcloned into plasmid vector pCR2.1-TOPO (Invitrogen) to determine their nucleotide sequences. The sequences of the two PCR products were identical (SEQ ID NO: 26).

The genetic information on the N-terminus of rat BG37 fragment was obtained by 5'-RACE and nested-PCR. First, 5'-RACE was carried out using primer rBG37-10R (5'-GG-GAGCTGCAGTTGGCACCAGGACTCCAG -3'/SEQ ID NO: 27) and marathon ready rat liver cDNA library (CLONTECH). Then, nested-PCR was carried out using the PCR product as a template with primer rBG37-8R (5'-GCAA-CACTGCCATGTAGCGTTCCCCATGCACC-3'/SEQ ID NO: 28). The PCR was carried out according to the protocol of AmpliTaq Gold from Perkin Elmer by heating at 95° C. for 9 minutes; 30 cycles of 94° C. for 30 seconds, 58° C. for 30 seconds, and 72° C. for 1 minutes; and finally heating at 94° C. for 30 seconds and at 62° C. for 10 minutes. The PCR product was subcloned into plasmid vector pCR2.1-TOPO (Invitrogen), and the nucleotide sequence was determined (SEQ ID NO: 29). Furthermore, to clone its upstream region, PCR was carried out with primer rBG37-14R (5'-CTGATGGCTCCTATTCCATAGCCC-3'/SEQ ID NO: 30) and the sequence of plasmid vector M13 Rev. (5'-CAGGAAACAGCTATGACC-3'/SEQ ID NO: 31) using a plasmid DNA purified from Superscript Rat Brain cDNA Library (LIFE TECHNOLOGIES) as the template DNA. The FOR was carried out using AmpliTaq Gold from Perkin Elmer by heating at 94° C. for 9 minutes; 39 cycles of 94° C. for 30 seconds, 50° C. for 15 seconds, and 72° C. for 60 seconds; and finally heating at 94° C. for 30 seconds and at 62° C. for 10 minutes. Then, nested-PCR was carried out with rBG37-13R (5'-TGTGAGTAGCCCAGCTAGTAGTAGGC-3'/SEQ ID NO: 32) using the PCR product as the template. The obtained PCR product was subcloned into plasmid vector pCR2.1-TOPO (Invitrogen), and the nucleotide sequence was determined (SEQ ID NO: 33).

In order to clone a cDNA containing the ORF of rat BG37, a fragment of interest was amplified by PCR using rat thalamus- and hypothalamus-derived cDNA libraries as templates with primers rBG37-16F (5'-GGATATCCATGATGTCACACAACACCACTG-3'/SEQ ID NO: 34) and rBG37-11R (5'-GGTCTGGGTGAGGTCTCATGGAGC-3'/SEQ ID NO: 35). Then, the PCR product was subcloned into plasmid vector pCR2.1-TOPO (Invitrogen) (pCR2.1-rBG37-G0703) to determine the nucleotide sequence of rat BG37 ORF (SEQ ID NO: 36).

The ORF was predicted to be 990 by (SEQ ID NO: 37) in length and was deduced to encode a protein of 329 amino acids (SEQ ID NO: 38). The degree of homology of the rat BG37 to human BG37 was found to be 84% at the DNA level and 82% at the amino acid level.

The E. coli strain containing the rat BG37 cDNA clone (E. coli rBG37-G0703) was deposited as follows:

(1) Name and Address of Depositary Institution

Name: International Patent Organism Depositary, National Institute of Advanced Industrial Science and Technology (AIST), Independent Administrative Institution (Previous Name: The National Institute of Bioscience and Human-Technology, The Agency of Industrial Science and Technology, The Ministry of International Trade and Industry)

Address: AIST Tsukuba Central 6, 1-1-1 Higashi, Tsukuba, Ibaraki, Japan (Zip code: 305-8566)

(2) Date of Deposition (Date of Initial Deposition): Feb. 20, 2001

(3) Accession Number: FERM BP-7741

Example 9

Expression Analysis of Rat BG37

Figure 5:
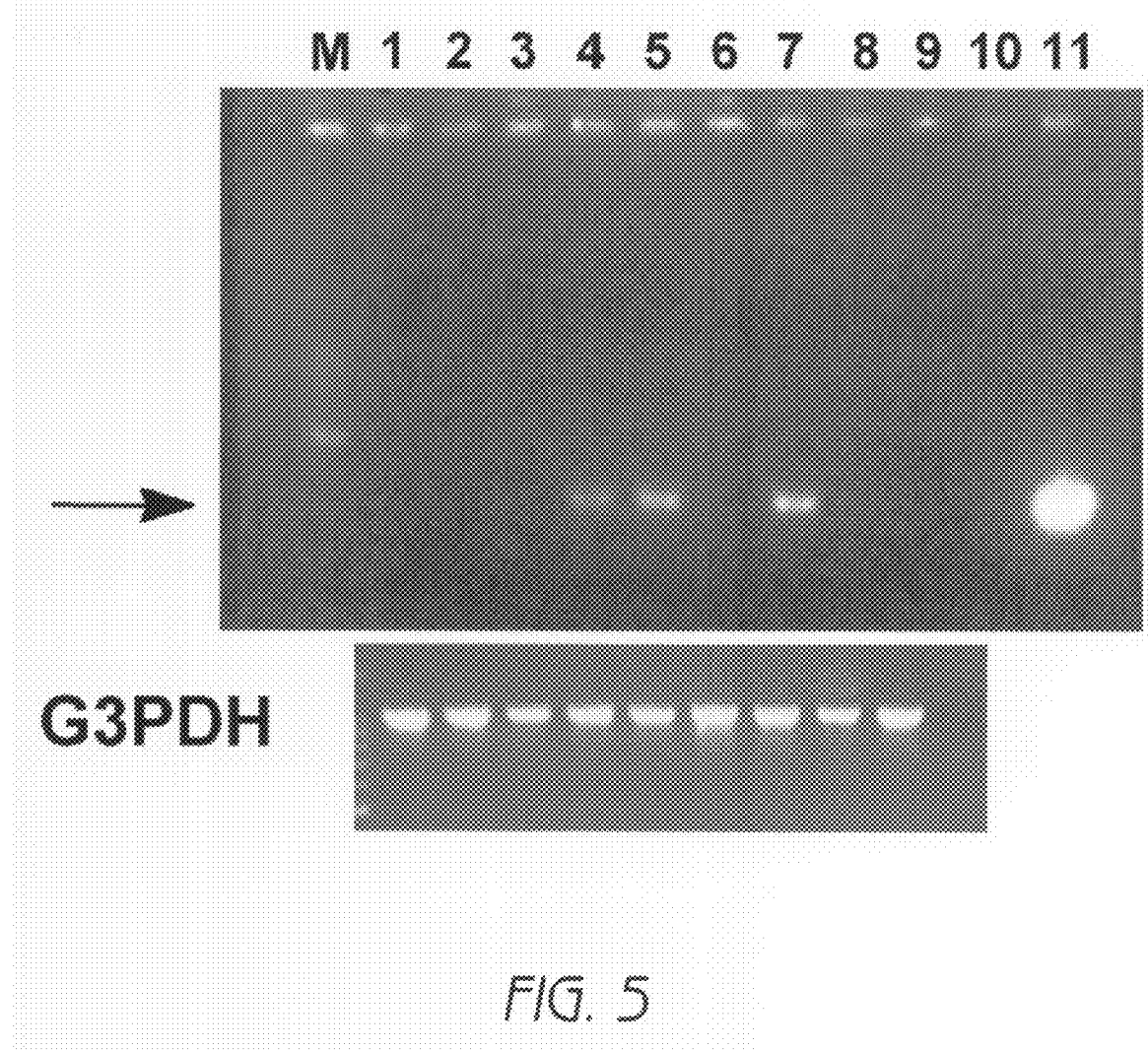
FIG. 5 depicts photographs. The upper photograph shows the result of testing the rat "BG37" expression site using rat MTC panel I. The lower photograph shows the result of detecting G3PDH expression in various tissues. Lanes 1 to 11 correspond to heart, brain, spleen, lung, liver, skeletal muscle, kidney, testis, negative control (no template), control cDNA (comprised in the kit), and rat genomic gene, respectively. Lane M corresponds to the size marker.

PCR was carried out using Multiple Tissue cDNA panel (rat MTC panel I, Clontech) to identify the expression sites of the rat BG37. The primers used were rBG37-3F and rBG37-12R. The PCR was carried out using AmpliTaq Gold from Perkin Elmer by heating at 94° C. for 9 minutes; 40 cycles of 94° C. for 30 seconds, 50° C. for 15 seconds, and 72° C. for 1 minutes; and finally heating at 94° C. for 30 seconds and at 62° C. for 10 minutes. FIG. 5 shows the result of electrophoresis of the PCR product on agarose gel. The size of the PCR product was about 312 bp. The rat BG37 was found to be expressed in the lung, liver, and kidney. No expression was detected in the heart, brain, spleen, skeletal muscle, and testis.

Example 10

Bile Acid-Dependent Increase of Intracellular cAMP Level

The intracellular cAMP levels were determined using the method of Zlokarmik et al. (Science 279, 84 (1998)). The intracellular cAMP level in the presence of a ligand was measured to determine the increase of the intracellular cAMP level through G proteins bound to the seven-transmembrane receptor.

On the day before the measurement of the intracellular cAMP level, cells were re-plated at a cell density of $4 \times 10^4$ cells/well on a poly-D-lysin-coated 96-well plate (Becton Dickinson), and then incubated at 37° C. for another 24 hours. Cells of the stable cell line were rinsed twice with 1 mM 3-Isobutyl-1-Methylxanthine (IBMX) (Nacalai Tesque) containing Opti-MEM solution (GIBCO BRL) (Opti-MEM-BSA-IBMX solution), and then incubated at 37° C. for 20 minutes. After removing the supernatant, Opti-MEM-IBMX solution containing a reagent at various concentrations was added thereto. The resulting mixture was incubated at 37° C. for 20 minutes. Then, the cells were lysed with 0.5% Triton X-100 to determine the level of intracellular cAMP.

Measurement of the intracellular cAMP level was carried out using cyclic AMP kit (HTRF) (Nihon Schering) according to the provided manual.

Figure 6:
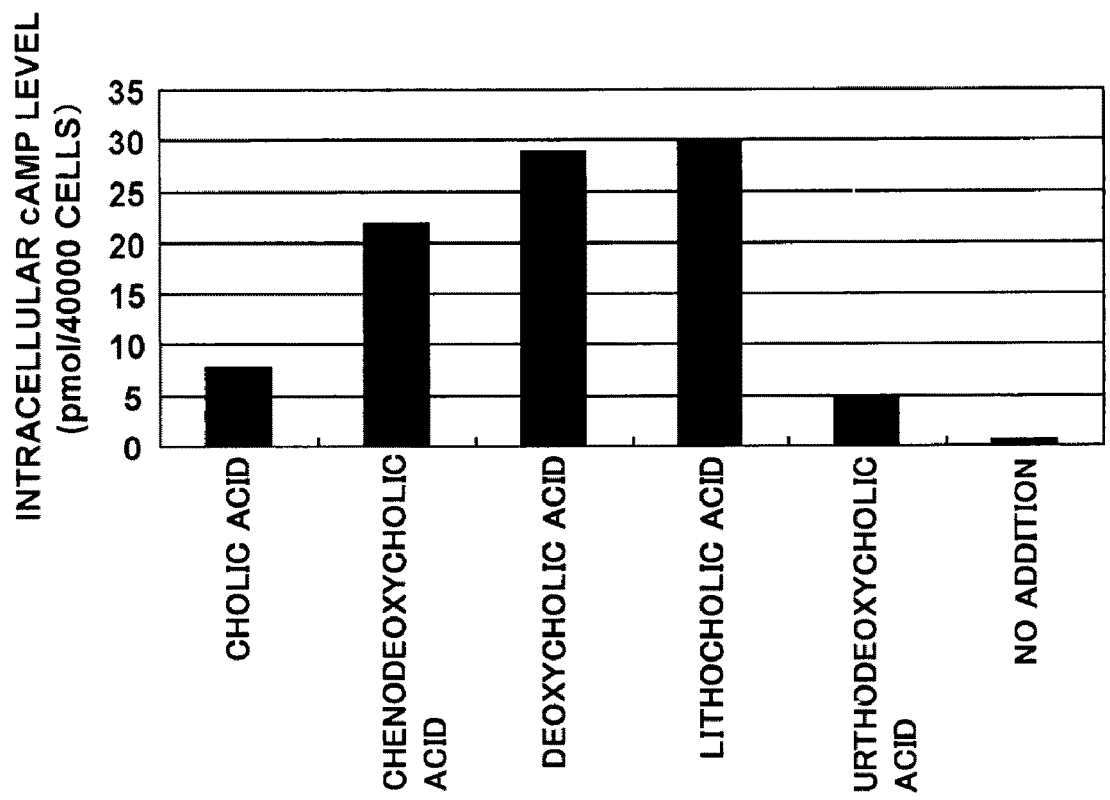
FIG. 6 is a graph showing the elevated intracellular cAMP level due to bile acid. The graph shows the intracellular cAMP level in HEK/hBG37 cells when the concentration of each compound was 10 μM.

Bile acids comprising a steroid backbone were tested to determine whether they activated the BG37 like the steroid hormones, such as progesterone. In cells expressing the human BG37, the intracellular cAMP level was elevated by cholic acid, chenodeoxycholic acid, deoxycholic acid, lithocholic acid, and ursodeoxycholic acid, as well as respective glycine conjugates and taurine conjugates thereof. The above-mentioned compounds did not increase the intracellular cAMP level in mock-transfected cells which expressed the vector alone. These findings showed that the bile acids, such as cholic acid, also specifically increases the intracellular cAMP level via the BG37. FIG. 6 shows the intracellular cAMP level in HEK/hBG37 cells when each of the concentration of the compounds was 10 μM.

INDUSTRIAL APPLICABILITY

The present invention provides novel G protein-coupled receptor proteins and genes encoding the proteins which are expressed in multiple tissues. The present invention enables screening of candidate compounds of ligands and pharmaceuticals using the receptor proteins. Such candidate compounds of ligands and pharmaceuticals are expected to be used, for example, to diagnose and treat diseases caused by abnormalities in the signaling system via the G protein-coupled receptor protein of the present invention.

The invention claimed is:

1. A method of screening for a compound having an activity to inhibit the binding between a protein peptide thereof and a ligand or analog thereof which binds to the protein wherein said protein is selected from the group consisting of
   (i) a protein comprising the amino acid sequence of SEQ ID NO: 2;
   (ii) a protein encoded by a DNA comprising the coding region of the nucleotide sequence of SEQ ID NO: 1;
   (iii) a protein comprising the amino acid sequence of SEQ ID NO: 2 with one to three amino acid substitutions, deletions, additions and/or insertions, wherein said protein is a guanosine triphosphate-binding protein-coupled receptor protein; and
   (iv) a protein is encoded by a DNA having a sequence that hybridizes to the DNA consisting of the nucleotide sequence of SEQ ID NO: 1, under conditions of hybridization in 6×SSC, 40% formamide at 25° C. and washing in 0.2×SSC at 55° C. wherein said DNA encodes a guanosine triphosphate-binding protein-coupled receptor which binds to one or more bile acid ligands selected from the group consisting of cholic acid, chenodeoxycholic acid, deoxycholic acid, and lithocholic acid, or the full complement of said DNA, and wherein said method comprises the steps of:
   (a) contacting a ligand or analog thereof which binds to the protein with the protein in the presence of a test compound, and detecting the binding activity of the protein to the ligand or analog thereof; and
   (b) comparing the binding activity detected in step (a) to that detected when the ligand or analog thereof is contacted with the protein in the absence of the test compound; and
   (c) selecting the compound which shows decreased binding activity between the protein and the ligand or analog thereof so compared in step (b).

2. The method according to claim 1, wherein the ligand is a biological substance having the steroid backbone.

3. The method according to claim 1, wherein the biological substance having the steroid backbone is selected from the group consisting of progesterone, dehydroisoandrosterone, testosterone, androstenedione, pregnenolone, cholic acid, chenodeoxycholic acid, deoxycholic acid, lithocholic acid, ursodeoxycholic acid, and 5.alpha.-dihydrotestosterone.

* * * * *

SEQUENCE LISTING

<160> NUMBER OF SEQ ID NOS: 38

<210> SEQ ID NO 1
<211> LENGTH: 993
<212> TYPE: DNA
<213> ORGANISM: Homo sapiens
<220> FEATURE:
<221> NAME/KEY: CDS
<222> LOCATION: (1)...(990)

<400> SEQUENCE: 1

| atg | acg | ccc | aac | agc | act | ggc | gag | gtg | ccc | agc | ccc | att | ccc | aag | ggg | 48 |
| Met | Thr | Pro | Asn | Ser | Thr | Gly | Glu | Val | Pro | Ser | Pro | Ile | Pro | Lys | Gly | |
| 1 | | | | 5 | | | | | 10 | | | | | 15 | | |

| gct | ttg | ggg | ctc | tcc | ctg | gcc | ctg | gca | agc | ctc | atc | atc | acc | gcg | aac | 96 |
| Ala | Leu | Gly | Leu | Ser | Leu | Ala | Leu | Ala | Ser | Leu | Ile | Ile | Thr | Ala | Asn | |
| | | | | 20 | | | | | 25 | | | | | 30 | | |

| ctc | cta | cta | gcc | ctg | ggc | atc | gcc | tgg | gac | cgc | cgc | ctg | cgc | agc | cca | 144 |
| Leu | Leu | Leu | Ala | Leu | Gly | Ile | Ala | Trp | Asp | Arg | Arg | Leu | Arg | Ser | Pro | |
| | | 35 | | | | | 40 | | | | | 45 | | | | |

| cct | gct | ggc | tgc | ttc | ttc | ctg | agc | cta | ctg | ctg | gct | ggg | ctg | ctc | acg | 192 |
| Pro | Ala | Gly | Cys | Phe | Phe | Leu | Ser | Leu | Leu | Leu | Ala | Gly | Leu | Leu | Thr | |
| | 50 | | | | | 55 | | | | | 60 | | | | | |

| ggt | ctg | gca | ttg | ccc | aca | ttg | cca | ggg | ctg | tgg | aac | cag | agt | cgc | cgg | 240 |
| Gly | Leu | Ala | Leu | Pro | Thr | Leu | Pro | Gly | Leu | Trp | Asn | Gln | Ser | Arg | Arg | |
| 65 | | | | | 70 | | | | | 75 | | | | | 80 | |

| ggt | tac | tgg | tcc | tgc | ctc | ctc | gtc | tac | ttg | gct | ccc | aac | ttc | tcc | ttc | 288 |
| Gly | Tyr | Trp | Ser | Cys | Leu | Leu | Val | Tyr | Leu | Ala | Pro | Asn | Phe | Ser | Phe | |
| | | | | 85 | | | | | 90 | | | | | 95 | | |

| ctc | tcc | ctg | ctt | gcc | aac | ctc | ttg | ctg | gtg | cac | ggg | gag | cgc | tac | atg | 336 |
| Leu | Ser | Leu | Leu | Ala | Asn | Leu | Leu | Leu | Val | His | Gly | Glu | Arg | Tyr | Met | |
| | | | | 100 | | | | | 105 | | | | | 110 | | |

| gca | gtc | ctg | agg | cca | ctc | cag | ccc | cct | ggg | agc | att | cgg | ctg | gcc | ctg | 384 |
| Ala | Val | Leu | Arg | Pro | Leu | Gln | Pro | Pro | Gly | Ser | Ile | Arg | Leu | Ala | Leu | |
| | | | 115 | | | | | 120 | | | | | 125 | | | |

| ctc | ctc | acc | tgg | gct | ggt | ccc | ctg | ctc | ttt | gcc | agt | ctg | ccc | gct | ctg | 432 |
| Leu | Leu | Thr | Trp | Ala | Gly | Pro | Leu | Leu | Phe | Ala | Ser | Leu | Pro | Ala | Leu | |
| | 130 | | | | | 135 | | | | | 140 | | | | | |

| ggg | tgg | aac | cac | tgg | acc | cct | ggt | gcc | aac | tgc | agc | tcc | cag | gct | atc | 480 |
| Gly | Trp | Asn | His | Trp | Thr | Pro | Gly | Ala | Asn | Cys | Ser | Ser | Gln | Ala | Ile | |
| 145 | | | | | 150 | | | | | 155 | | | | | 160 | |

| ttc | cca | gcc | ccc | tac | ctg | tac | ctc | gaa | gtc | tat | ggg | ctc | ctg | ctg | ccc | 528 |
| Phe | Pro | Ala | Pro | Tyr | Leu | Tyr | Leu | Glu | Val | Tyr | Gly | Leu | Leu | Leu | Pro | |
| | | | | 165 | | | | | 170 | | | | | 175 | | |

| gcc | gtg | ggt | gct | gct | gcc | ttc | ctc | tct | gtc | cgc | gtg | ctg | gcc | act | gcc | 576 |
| Ala | Val | Gly | Ala | Ala | Ala | Phe | Leu | Ser | Val | Arg | Val | Leu | Ala | Thr | Ala | |
| | | | 180 | | | | | 185 | | | | | 190 | | | |

| cac | cgc | cag | ctg | cag | gac | atc | tgc | cgg | ctg | gag | cgg | gca | gtg | tgc | cgc | 624 |
| His | Arg | Gln | Leu | Gln | Asp | Ile | Cys | Arg | Leu | Glu | Arg | Ala | Val | Cys | Arg | |
| | | | | 195 | | | | | 200 | | | | | 205 | | |

| gat | gag | ccc | tcc | gcc | ctg | gcc | cgg | gcc | ctt | acc | tgg | agg | cag | gca | agg | 672 |
| Asp | Glu | Pro | Ser | Ala | Leu | Ala | Arg | Ala | Leu | Thr | Trp | Arg | Gln | Ala | Arg | |
| | | 210 | | | | | 215 | | | | | 220 | | | | |

| gca | cag | gct | gga | gcc | atg | ctg | ctc | ttc | ggg | ctg | tgc | tgg | ggg | ccc | tac | 720 |
| Ala | Gln | Ala | Gly | Ala | Met | Leu | Leu | Phe | Gly | Leu | Cys | Trp | Gly | Pro | Tyr | |
| 225 | | | | | 230 | | | | | 235 | | | | | 240 | |

| gtg | gcc | aca | ctg | ctc | ctc | tca | gtc | ctg | gcc | tat | gag | cag | cgc | ccg | cca | 768 |
| Val | Ala | Thr | Leu | Leu | Leu | Ser | Val | Leu | Ala | Tyr | Glu | Gln | Arg | Pro | Pro | |
| | | | | 245 | | | | | 250 | | | | | 255 | | |

```
ctg ggg cct ggg aca ctg ttg tcc ctc ctc tcc cta gga agt gcc agt     816
Leu Gly Pro Gly Thr Leu Leu Ser Leu Leu Ser Leu Gly Ser Ala Ser
        260                 265                 270 gca gcg gca gtg ccc gta gcc atg ggg ctg ggc gat cag cgc tac aca     864
Ala Ala Ala Val Pro Val Ala Met Gly Leu Gly Asp Gln Arg Tyr Thr
            275                 280                 285 gcc ccc tgg agg gca gcc gcc caa agg tgc ctg cag ggg ctg tgg gga     912
Ala Pro Trp Arg Ala Ala Ala Gln Arg Cys Leu Gln Gly Leu Trp Gly
    290                 295                 300 aga gcc tcc cgg gac agt ccc ggc ccc agc att gcc tac cac cca agc     960
Arg Ala Ser Arg Asp Ser Pro Gly Pro Ser Ile Ala Tyr His Pro Ser
305                 310                 315                 320 agc caa agc agt gtc gac ctg gac ttg aac taa                         993
Ser Gln Ser Ser Val Asp Leu Asp Leu Asn
                325                 330

<210> SEQ ID NO 2
<211> LENGTH: 330
<212> TYPE: PRT
<213> ORGANISM: Homo sapiens

<400> SEQUENCE: 2

Met Thr Pro Asn Ser Thr Gly Glu Val Pro Ser Pro Ile Pro Lys Gly
 1               5                  10                  15

Ala Leu Gly Leu Ser Leu Ala Leu Ala Ser Leu Ile Ile Thr Ala Asn
            20                  25                  30

Leu Leu Leu Ala Leu Gly Ile Ala Trp Asp Arg Arg Leu Arg Ser Pro
        35                  40                  45

Pro Ala Gly Cys Phe Phe Leu Ser Leu Leu Ala Gly Leu Leu Thr
    50                  55                  60

Gly Leu Ala Leu Pro Thr Leu Pro Gly Leu Trp Asn Gln Ser Arg Arg
 65                  70                  75                  80

Gly Tyr Trp Ser Cys Leu Leu Val Tyr Leu Ala Pro Asn Phe Ser Phe
                85                  90                  95

Leu Ser Leu Leu Ala Asn Leu Leu Leu Val His Gly Glu Arg Tyr Met
            100                 105                 110

Ala Val Leu Arg Pro Leu Gln Pro Pro Gly Ser Ile Arg Leu Ala Leu
        115                 120                 125

Leu Leu Thr Trp Ala Gly Pro Leu Leu Phe Ala Ser Leu Pro Ala Leu
    130                 135                 140

Gly Trp Asn His Trp Thr Pro Gly Ala Asn Cys Ser Ser Gln Ala Ile
145                 150                 155                 160

Phe Pro Ala Pro Tyr Leu Tyr Leu Glu Val Tyr Gly Leu Leu Leu Pro
                165                 170                 175

Ala Val Gly Ala Ala Phe Leu Ser Val Arg Val Leu Ala Thr Ala
            180                 185                 190

His Arg Gln Leu Gln Asp Ile Cys Arg Leu Glu Arg Ala Val Cys Arg
        195                 200                 205

Asp Glu Pro Ser Ala Leu Ala Arg Ala Leu Thr Trp Arg Gln Ala Arg
    210                 215                 220

Ala Gln Ala Gly Ala Met Leu Leu Phe Gly Leu Cys Trp Gly Pro Tyr
225                 230                 235                 240

Val Ala Thr Leu Leu Leu Ser Val Leu Ala Tyr Glu Gln Arg Pro Pro
                245                 250                 255

Leu Gly Pro Gly Thr Leu Leu Ser Leu Leu Ser Leu Gly Ser Ala Ser
            260                 265                 270
```

```
Ala Ala Ala Val Pro Val Ala Met Gly Leu Gly Asp Gln Arg Tyr Thr
        275                 280                 285

Ala Pro Trp Arg Ala Ala Gln Arg Cys Leu Gln Gly Leu Trp Gly
    290                 295                 300

Arg Ala Ser Arg Asp Ser Pro Gly Pro Ser Ile Ala Tyr His Pro Ser
305                 310                 315                 320

Ser Gln Ser Ser Val Asp Leu Asp Leu Asn
                325                 330

<210> SEQ ID NO 3
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 3
ctacatggca gtcctgaggc                                                      20

<210> SEQ ID NO 4
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 4
actgagagga gcagtgtggc                                                      20

<210> SEQ ID NO 5
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 5
cgtggccaca ctgctcctct cagtc                                                25

<210> SEQ ID NO 6
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 6
cccctgtccc caggaccaag atg                                                  23

<210> SEQ ID NO 7
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 7
ttagttcaag tccaggtcga cactgcttt                                            29

<210> SEQ ID NO 8
<211> LENGTH: 25
<212> TYPE: DNA
<213> ORGANISM: Artificial Sequence
<220> FEATURE:
<223> OTHER INFORMATION: Artificially Synthesized Primer Sequence
```

<400> SEQUENCE: 8
ctgcctcctc gtctacttgg ctccc                                          25

<210> SEQ ID NO 9
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 9
tgagaggagc agtgtggcca cgtagggc                                       28

<210> SEQ ID NO 10
<211> LENGTH: 437
<212> TYPE: DNA
<213> ORGANISM: Mus musculus

<400> SEQUENCE: 10 aactttttgtt tccttttccct gcttgccaat ctgctgctgg tgcatgggga acgctacatg    60
gcagtgttgc agccactccg gccccatgga agtgtgcggc tagccctgtt cctcacctgg   120
gtcagctccc tgttctttgc cagcctgcct gctctgggct ggaaccattg gagccctgat   180
gccaactgca gctcccaagc tgtcttccca gccccctacc tctacctgga agtttatggc   240
ctcctgttgc ctgccgtggg ggccactgcc cttctctctg tccgcgtgtt ggccactgcc   300
caccgccagc tgtgtgagat ccgccgactg gagcgggcag tgtgccgcga tgtaccctca   360
accctggcta gggctctcac ctggaggcag gctagggcac aggcaggagc cacactgctc   420
ttcttgctgt gttgggg                                                  437

<210> SEQ ID NO 11
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 11
ccctcaaccc tggctagggc tctcacc                                        27

<210> SEQ ID NO 12
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 12
gccacactgc tcttcttgct gtgttgggg                                      29

<210> SEQ ID NO 13
<211> LENGTH: 309
<212> TYPE: DNA
<213> ORGANISM: Mus musculus

<400> SEQUENCE: 13
gccacactgc tcttcttgct gtgttggggg ccctatgtgg ccacattgct cctgtcagtc    60
ttggcctatg agcgtcgccc accactaggg cctggaactc tgttatcgct catctcattg   120
ggcagcacca gtgctgccgc tgtgcctgtg gccatggggc tgggtgatca gcgctacaca   180

```
gccccctgga ggacagctgc ccaaaggtgt ctacgagtgc ttcgaggaag agccaagagg    240
gacaatccag gccccagcac tgcctaccac accagtagcc aatgcagcat tgacctggac    300
ttgaattag                                                            309
```

```
<210> SEQ ID NO 14
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 14
gctgacccag gtgaggaaca gggctagccg c                                    31
```

```
<210> SEQ ID NO 15
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 15
gcagattggc aagcagggaa aggaaacaaa ag                                   32
```

```
<210> SEQ ID NO 16
<211> LENGTH: 319
<212> TYPE: DNA
<213> ORGANISM: Mus musculus

<400> SEQUENCE: 16
gtgccaagac ccatgatgac acccaacagc actgagctgt cggccattcc catgggggtt     60
ctggggcttt ccttggccct ggcaagcctc atcgtcatcg ccaacctgct cctggcccta    120
ggcatcgccc tggaccgcca cttgcgcagc ccacctgctg gctgcttctt cctaagccta    180
ctactagccg ggctgctcac agggctggca ctgcccatgc tgcctgggct atggagccgg    240
aaccatcagg gctactggtc ctgcctcctt ctccacttga cccccaactt ttgtttcctt    300
tccctgcttg ccaatctgc                                                 319
```

```
<210> SEQ ID NO 17
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 17
gtgccaagac ccatgatgac accc                                            24
```

```
<210> SEQ ID NO 18
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 18
ctaattcaag tccaggtcaa tgctgc                                          26
```

```
<210> SEQ ID NO 19
<211> LENGTH: 990
<212> TYPE: DNA
<213> ORGANISM: Mus musculus
```

<220> FEATURE:
<221> NAME/KEY: CDS
<222> LOCATION: (1)...(987)

<400> SEQUENCE: 19

```
atg atg aca ccc aac agc act gag ctg tcg gcc att ccc atg ggg gtt        48
Met Met Thr Pro Asn Ser Thr Glu Leu Ser Ala Ile Pro Met Gly Val
1               5                   10                  15 ctg ggg ctt tcc ttg gcc ctg gca agc ctc atc gtc atc gcc aac ctg        96
Leu Gly Leu Ser Leu Ala Leu Ala Ser Leu Ile Val Ile Ala Asn Leu
                20                  25                  30 ctc ctg gcc cta ggc atc gcc ctg gac cgc cac ttg cgc agc cca cct       144
Leu Leu Ala Leu Gly Ile Ala Leu Asp Arg His Leu Arg Ser Pro Pro
            35                  40                  45 gct ggc tgc ttc ttc cta agc cta cta cta gcc ggg ctg ctc aca ggg       192
Ala Gly Cys Phe Phe Leu Ser Leu Leu Leu Ala Gly Leu Leu Thr Gly
        50                  55                  60 ctg gca ctg ccc atg ctg cct ggg cta tgg agc cgg aac cat cag ggc       240
Leu Ala Leu Pro Met Leu Pro Gly Leu Trp Ser Arg Asn His Gln Gly
65                  70                  75                  80 tac tgg tcc tgc ctc ctt ctc cac ttg acc ccc aac ttt tgt ttc ctt       288
Tyr Trp Ser Cys Leu Leu Leu His Leu Thr Pro Asn Phe Cys Phe Leu
                85                  90                  95 tcc ctg ctt gcc aat ctg ctg ctg gtg cat ggg gaa cgc tac atg gca       336
Ser Leu Leu Ala Asn Leu Leu Leu Val His Gly Glu Arg Tyr Met Ala
                100                 105                 110 gtg ttg cag cca ctc cgg ccc cat gga agt gtg cgg cta gcc ctg ttc       384
Val Leu Gln Pro Leu Arg Pro His Gly Ser Val Arg Leu Ala Leu Phe
            115                 120                 125 ctc acc tgg gtc agc tcc ctg ttc ttt gcc agc ctg cct gct ctg ggc       432
Leu Thr Trp Val Ser Ser Leu Phe Phe Ala Ser Leu Pro Ala Leu Gly
        130                 135                 140 tgg aac cat tgg agc cct gat gcc aac tgc agc tcc caa gct gtc ttc       480
Trp Asn His Trp Ser Pro Asp Ala Asn Cys Ser Ser Gln Ala Val Phe
145                 150                 155                 160 cca gcc ccc tac ctc tac ctg gaa gtt tat ggc ctc ctg ttg cct gcc       528
Pro Ala Pro Tyr Leu Tyr Leu Glu Val Tyr Gly Leu Leu Leu Pro Ala
                165                 170                 175 gtg ggg gcc act gcc ctt ctc tct gtc cgc gtg ttg gcc act gcc cac       576
Val Gly Ala Thr Ala Leu Leu Ser Val Arg Val Leu Ala Thr Ala His
                180                 185                 190 cgc cag ctg tgt gag atc cgc cga ctg gag cgg gca gtg tgc cgc gat       624
Arg Gln Leu Cys Glu Ile Arg Arg Leu Glu Arg Ala Val Cys Arg Asp
            195                 200                 205 gta ccc tca acc ctg gct agg gct ctc acc tgg agg cag gct agg gca       672
Val Pro Ser Thr Leu Ala Arg Ala Leu Thr Trp Arg Gln Ala Arg Ala
        210                 215                 220 cag gca gga gcc aca ctg ctc ttc ttg ctg tgt tgg ggg ccc tat gtg       720
Gln Ala Gly Ala Thr Leu Leu Phe Leu Leu Cys Trp Gly Pro Tyr Val
225                 230                 235                 240 gcc aca ttg ctc ctg tca gtc ttg gcc tat gag cgt cgc cca cca cta       768
Ala Thr Leu Leu Leu Ser Val Leu Ala Tyr Glu Arg Arg Pro Pro Leu
                245                 250                 255 ggg cct gga act ctg tta tcg ctc atc tca ttg ggc agc acc agt gct       816
Gly Pro Gly Thr Leu Leu Ser Leu Ile Ser Leu Gly Ser Thr Ser Ala
                260                 265                 270 gcc gct gtg cct gtg gcc atg ggg ctg ggt gat cag cgc tac aca gcc       864
Ala Ala Val Pro Val Ala Met Gly Leu Gly Asp Gln Arg Tyr Thr Ala
            275                 280                 285 ccc tgg agg aca gct gcc caa agg tgt cta cga gtg ctt cga gga aga       912
```

```
Pro Trp Arg Thr Ala Ala Gln Arg Cys Leu Arg Val Leu Arg Gly Arg
    290                 295                 300 gcc aag agg gac aat cca ggc ccc agc act gcc tac cac acc agt agc    960
Ala Lys Arg Asp Asn Pro Gly Pro Ser Thr Ala Tyr His Thr Ser Ser
305                 310                 315                 320 caa tgc agc att gac ctg gac ttg aat tag                            990
Gln Cys Ser Ile Asp Leu Asp Leu Asn
                325

<210> SEQ ID NO 20
<211> LENGTH: 329
<212> TYPE: PRT
<213> ORGANISM: Mus musculus

<400> SEQUENCE: 20

Met Met Thr Pro Asn Ser Thr Glu Leu Ser Ala Ile Pro Met Gly Val
  1               5                  10                  15

Leu Gly Leu Ser Leu Ala Leu Ala Ser Leu Ile Val Ile Ala Asn Leu
                 20                  25                  30

Leu Leu Ala Leu Gly Ile Ala Leu Asp Arg His Leu Arg Ser Pro Pro
             35                  40                  45

Ala Gly Cys Phe Phe Leu Ser Leu Leu Ala Gly Leu Leu Thr Gly
         50                  55                  60

Leu Ala Leu Pro Met Leu Pro Gly Leu Trp Ser Arg Asn His Gln Gly
 65                  70                  75                  80

Tyr Trp Ser Cys Leu Leu His Leu Thr Pro Asn Phe Cys Phe Leu
                 85                  90                  95

Ser Leu Leu Ala Asn Leu Leu Leu Val His Gly Glu Arg Tyr Met Ala
                100                 105                 110

Val Leu Gln Pro Leu Arg Pro His Gly Ser Val Arg Leu Ala Leu Phe
            115                 120                 125

Leu Thr Trp Val Ser Ser Leu Phe Phe Ala Ser Leu Pro Ala Leu Gly
        130                 135                 140

Trp Asn His Trp Ser Pro Asp Ala Asn Cys Ser Ser Gln Ala Val Phe
145                 150                 155                 160

Pro Ala Pro Tyr Leu Tyr Leu Glu Val Tyr Gly Leu Leu Pro Ala
                165                 170                 175

Val Gly Ala Thr Ala Leu Leu Ser Val Arg Val Leu Ala Thr Ala His
            180                 185                 190

Arg Gln Leu Cys Glu Ile Arg Arg Leu Glu Arg Ala Val Cys Arg Asp
        195                 200                 205

Val Pro Ser Thr Leu Ala Arg Ala Leu Thr Trp Arg Gln Ala Arg Ala
    210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Gly Thr Leu Leu Ser Leu Ile Ser Leu Gly Ser Thr Ser Ala
            260                 265                 270

Ala Ala Val Pro Val Ala Met Gly Leu Gly Asp Gln Arg Tyr Thr Ala
        275                 280                 285

Pro Trp Arg Thr Ala Ala Gln Arg Cys Leu Arg Val Leu Arg Gly Arg
    290                 295                 300

Ala Lys Arg Asp Asn Pro Gly Pro Ser Thr Ala Tyr His Thr Ser Ser
305                 310                 315                 320
```

Gln Cys Ser Ile Asp Leu Asp Leu Asn
                  325

<210> SEQ ID NO 21
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 21
ttccctgctt gccaatctgc tgctgg                                26

<210> SEQ ID NO 22
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 22
cacagcaaga agagcagtgt ggctcc                                26

<210> SEQ ID NO 23
<211> LENGTH: 437
<212> TYPE: DNA
<213> ORGANISM: Rattus norvegicus

<400> SEQUENCE: 23
aacttttgtt tcctctccct gcttgccaat ctgctgctgg tgcatgggga acgctacatg    60
gcagtgttgc agccactccg gccccatggg agtgtgcggc tagccctgtt cctcacctgg   120
atcagctccc tgctctttgc cagcctgcct gctctgggct ggaaccactg gagtcctggt   180
gccaactgca gctcccaggc tatcttccca gcccctacc tttacctcga agtctatggg   240
ctcctgctgc ccgctgtggg ggccactgcc cttctctctg tccgagtgtt ggccactgcc   300
caccaccagc tgcgggagat ccgcagactg gagcgggcgg tgtgccgtga tgcaccctca   360
accctagcga gggctctcac ctggaggcag gctagggcac aggcaggagc cacactgctc   420
tttttgctgt gttgggg                                                    437

<210> SEQ ID NO 24
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 24
ccctaattca agtccaagtc agtg                                    24

<210> SEQ ID NO 25
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 25
gccacactgc tcttttgct gtgttgggg                              29

<210> SEQ ID NO 26
<211> LENGTH: 311
<212> TYPE: DNA

<213> ORGANISM: Rattus norvegicus

<400> SEQUENCE: 26

```
gccacactgc tcttttgct gtgttgggg ccctatgtgg ccacattgct cctgtcagtc    60
ttggcctatg agcggcggcc accactaggg cctgtaactc tgttatctct catctcattg  120
ggcagtgcca gtgctgcagt tgtgcctgtg ccatgggtc tgggtgatca gcgctacacg  180
gccccctgga ggacagctgc ccaaaggtgg ctacaagtgc ttcgaggaag acccaagagg  240
gccaatccag gccccagcac tgcctaccac tccagtagcc aatgcagcac tgacttggac  300
ttgaattagg g                                                       311
```

<210> SEQ ID NO 27
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 27

```
gggagctgca gttggcacca ggactccag                                     29
```

<210> SEQ ID NO 28
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 28

```
gcaacactgc catgtagcgt tccccatgca cc                                 32
```

<210> SEQ ID NO 29
<211> LENGTH: 196
<212> TYPE: DNA
<213> ORGANISM: Rattus norvegicus

<400> SEQUENCE: 29

```
ggctgcttct ttctaagcct actactagct gggctactca cagggttggc actgcccacg    60
ctgcctgggc tatggaatag gagccatcag gggtactggt cctgcctcct tctccacttg  120
gcccccaact tttgtttcct ctccctgctt gccaatctgc tgctggtgca tggggaacgc  180
tacatggcag tgttgc                                                  196
```

<210> SEQ ID NO 30
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 30

```
ctgatggctc ctattccata gccc                                          24
```

<210> SEQ ID NO 31
<211> LENGTH: 18
<212> TYPE: DNA
<213> ORGANISM: Artificial Sequence
<220> FEATURE:
<223> OTHER INFORMATION: Artificially Synthesized Primer Sequence

<400> SEQUENCE: 31

```
caggaaacag ctatgacc                                                 18
```

<210> SEQ ID NO 32
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 32
tgtgagtagc ccagctagta gtaggc                                   26

<210> SEQ ID NO 33
<211> LENGTH: 255
<212> TYPE: DNA
<213> ORGANISM: Rattus norvegicus

<400> SEQUENCE: 33
gcactacctg ttcctaacag ccatgcatgc tggctgcagc tccggaccct ccatgcgcca   60
agacccatga tgtcacacaa caccactgag ctgtcagcca ttcccagagg ggttcaggag  120
ctttccctgg tcctggcaag cctcatcgtc atcgccaacc tgctcctggc cctaggcatt  180
gtcctggacc gccacttacg cagcccacct gctggctgct tctttctaag cctactacta  240
gctgggctac tcaca                                                  255

<210> SEQ ID NO 34
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 34
ggatatccat gatgtcacac aacaccactg                               30

<210> SEQ ID NO 35
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 35
ggtctgggtg aggtctcatg gagc                                     24

<210> SEQ ID NO 36
<211> LENGTH: 1098
<212> TYPE: DNA
<213> ORGANISM: Rattus norvegicus

<400> SEQUENCE: 36
ggatatccat gatgtcacac aacaccactg agctgtcagc cattcccaga ggggttcagg   60
agctttccct ggtcctggca agcctcatcg tcatcgccaa cctgctcctg gccctaggca  120
ttgtcctgga ccgccactta cgcagcccac tgctggctg cttctttcta agcctactac  180
tagctgggct actcacaggg ttggcactgc ccacgctgcc tgggctatgg aataggagcc  240
atcaggggta ctggtcctgc ctccttctcc acttggcccc caacttttgt ttcctctccc  300
tgcttgccaa tctgctgctg gtgcatgggg aacgctacat ggcagtgttg cagccactcc  360
ggccccatgg gagtgtgcgg ctagccctgt tcctcacctg gatcagctcc ctgtctcttt  420
ccagcctgcc tgtctctggc tggaaccact ggagtcctgg tgccaactgc agctcccagg  480

```
ctatcttccc agcccctac ctttacctcg aagtctatgg gctcctgctg cccgctgtgg      540
gggccactgc ccttctctct gtccgagtgt tggccactgc ccaccaccag ctgcgggaga      600
tccgcagact ggagcgggcg gtgtgccgtg atgcaccctc aaccctagcg agggctctca      660
cctggaggca ggctagggca caggcaggag ccacactgct ctttttgctg tgttgggggc      720
cctatgtggc cacattgctc ctgtcagtct tggcctatga gcggcggcca ccactagggc      780
ctgtaactct gttatctctc atctcattgg gcagtgccag tgctgcagtt gtgcctgtgg      840
ccatgggtct gggtgatcag cgctacacgg cccctggag gacagctgcc caaaggtggc      900
tacaagtgct tcgaggaaga cccaagaggg ccaatccagg ccccagcact gcctaccact      960
ccagtagcca atgcagcact gacttggact tgaattaggg aaacagtagc tactgctgcc     1020
tcccaggaca cacatctatc tcatagtgcc ccacttcttt ggcttggagc ccttgctcca     1080
tgagacctca cccagacc                                                  1098

<210> SEQ ID NO 37
<211> LENGTH: 990
<212> TYPE: DNA
<213> ORGANISM: Rattus norvegicus
<220> FEATURE:
<221> NAME/KEY: CDS
<222> LOCATION: (1)...(987)

<400> SEQUENCE: 37 atg atg tca cac aac acc act gag ctg tca gcc att ccc aga ggg gtt       48
Met Met Ser His Asn Thr Thr Glu Leu Ser Ala Ile Pro Arg Gly Val
1               5                   10                  15 cag gag ctt tcc ctg gtc ctg gca agc ctc atc gtc atc gcc aac ctg       96
Gln Glu Leu Ser Leu Val Leu Ala Ser Leu Ile Val Ile Ala Asn Leu
            20                  25                  30 ctc ctg gcc cta ggc att gtc ctg gac cgc cac tta cgc agc cca cct      144
Leu Leu Ala Leu Gly Ile Val Leu Asp Arg His Leu Arg Ser Pro Pro
        35                  40                  45 gct ggc tgc ttc ttt cta agc cta cta cta gct ggg cta ctc aca ggg      192
Ala Gly Cys Phe Phe Leu Ser Leu Leu Leu Ala Gly Leu Leu Thr Gly
    50                  55                  60 ttg gca ctg ccc acg ctg cct ggg cta tgg aat agg agc cat cag ggg      240
Leu Ala Leu Pro Thr Leu Pro Gly Leu Trp Asn Arg Ser His Gln Gly
65                  70                  75                  80 tac tgg tcc tgc ctc ctt ctc cac ttg gcc ccc aac ttt tgt ttc ctc      288
Tyr Trp Ser Cys Leu Leu Leu His Leu Ala Pro Asn Phe Cys Phe Leu
                85                  90                  95 tcc ctg ctt gcc aat ctg ctg ctg gtg cat ggg gaa cgc tac atg gca      336
Ser Leu Leu Ala Asn Leu Leu Leu Val His Gly Glu Arg Tyr Met Ala
            100                 105                 110 gtg ttg cag cca ctc cgg ccc cat ggg agt gtg cgg cta gcc ctg ttc      384
Val Leu Gln Pro Leu Arg Pro His Gly Ser Val Arg Leu Ala Leu Phe
        115                 120                 125 ctc acc tgg atc agc tcc ctg ctc ttt gcc agc ctg cct gct ctg ggc      432
Leu Thr Trp Ile Ser Ser Leu Leu Phe Ala Ser Leu Pro Ala Leu Gly
    130                 135                 140 tgg aac cac tgg agt cct ggt gcc aac tgc agc tcc cag gct atc ttc      480
Trp Asn His Trp Ser Pro Gly Ala Asn Cys Ser Ser Gln Ala Ile Phe
145                 150                 155                 160 cca gcc ccc tac ctt tac ctc gaa gtc tat ggg ctc ctg ctg ccc gct      528
Pro Ala Pro Tyr Leu Tyr Leu Glu Val Tyr Gly Leu Leu Leu Pro Ala
                165                 170                 175 gtg ggg gcc act gcc ctt ctc tct gtc cga gtg ttg gcc act gcc cac      576
Val Gly Ala Thr Ala Leu Leu Ser Val Arg Val Leu Ala Thr Ala His
            180                 185                 190
```

```
           180                 185                 190
cac cag ctg cgg gag atc cgc aga ctg gag cgg gcg gtg tgc cgt gat   624
His Gln Leu Arg Glu Ile Arg Arg Leu Glu Arg Ala Val Cys Arg Asp
            195                 200                 205 gca ccc tca acc cta gcg agg gct ctc acc tgg agg cag gct agg gca   672
Ala Pro Ser Thr Leu Ala Arg Ala Leu Thr Trp Arg Gln Ala Arg Ala
    210                 215                 220 cag gca gga gcc aca ctg ctc ttt ttg ctg tgt tgg ggg ccc tat gtg   720
Gln Ala Gly Ala Thr Leu Leu Phe Leu Leu Cys Trp Gly Pro Tyr Val
225                 230                 235                 240 gcc aca ttg ctc ctg tca gtc ttg gcc tat gag cgg cgg cca cca cta   768
Ala Thr Leu Leu Leu Ser Val Leu Ala Tyr Glu Arg Arg Pro Pro Leu
                245                 250                 255 ggg cct gta act ctg tta tct ctc atc tca ttg ggc agt gcc agt gct   816
Gly Pro Val Thr Leu Leu Ser Leu Ile Ser Leu Gly Ser Ala Ser Ala
            260                 265                 270 gca gtt gtg cct gtg gcc atg ggt ctg ggt gat cag cgc tac acg gcc   864
Ala Val Val Pro Val Ala Met Gly Leu Gly Asp Gln Arg Tyr Thr Ala
        275                 280                 285 ccc tgg agg aca gct gcc caa agg tgg cta caa gtg ctt cga gga aga   912
Pro Trp Arg Thr Ala Ala Gln Arg Trp Leu Gln Val Leu Arg Gly Arg
    290                 295                 300 ccc aag agg gcc aat cca ggc ccc agc act gcc tac cac tcc agt agc   960
Pro Lys Arg Ala Asn Pro Gly Pro Ser Thr Ala Tyr His Ser Ser Ser
305                 310                 315                 320 caa tgc agc act gac ttg gac ttg aat tag                           990
Gln Cys Ser Thr Asp Leu Asp Leu Asn
                325

<210> SEQ ID NO 38
<211> LENGTH: 329
<212> TYPE: PRT
<213> ORGANISM: Rattus norvegicus

<400> SEQUENCE: 38

Met Met Ser His Asn Thr Thr Glu Leu Ser Ala Ile Pro Arg Gly Val
1               5                   10                  15

Gln Glu Leu Ser Leu Val Leu Ala Ser Leu Ile Val Ile Ala Asn Leu
            20                  25                  30

Leu Leu Ala Leu Gly Ile Val Leu Asp Arg His Leu Arg Ser Pro Pro
        35                  40                  45

Ala Gly Cys Phe Phe Leu Ser Leu Leu Leu Ala Gly Leu Leu Thr Gly
    50                  55                  60

Leu Ala Leu Pro Thr Leu Pro Gly Leu Trp Asn Arg Ser His Gln Gly
65                  70                  75                  80

Tyr Trp Ser Cys Leu Leu His Leu Ala Pro Asn Phe Cys Phe Leu
                85                  90                  95

Ser Leu Leu Ala Asn Leu Leu Leu Val His Gly Glu Arg Tyr Met Ala
            100                 105                 110

Val Leu Gln Pro Leu Arg Pro His Gly Ser Val Arg Leu Ala Leu Phe
        115                 120                 125

Leu Thr Trp Ile Ser Ser Leu Leu Phe Ala Ser Leu Pro Ala Leu Gly
    130                 135                 140

Trp Asn His Trp Ser Pro Gly Ala Asn Cys Ser Ser Gln Ala Ile Phe
145                 150                 155                 160

Pro Ala Pro Tyr Leu Tyr Leu Glu Val Tyr Gly Leu Leu Leu Pro Ala
                165                 170                 175
```

-continued

```
Val Gly Ala Thr Ala Leu Leu Ser Val Arg Val Leu Ala Thr Ala His
            180                 185                 190

His Gln Leu Arg Glu Ile Arg Arg Leu Glu Arg Ala Val Cys Arg Asp
        195                 200                 205

Ala Pro Ser Thr Leu Ala Arg Ala Leu Thr Trp Arg Gln Ala Arg Ala
    210                 215                 220

Gln Ala Gly Ala Thr Leu Leu Phe Leu Leu Cys Trp Gly Pro Tyr Val
225                 230                 235                 240

Ala Thr Leu Leu Leu Ser Val Leu Ala Tyr Glu Arg Arg Pro Pro Leu
                245                 250                 255

Gly Pro Val Thr Leu Leu Ser Leu Ile Ser Leu Gly Ser Ala Ser Ala
            260                 265                 270

Ala Val Val Pro Val Ala Met Gly Leu Gly Asp Gln Arg Tyr Thr Ala
            275                 280                 285

Pro Trp Arg Thr Ala Ala Gln Arg Trp Leu Gln Val Leu Arg Gly Arg
        290                 295                 300

Pro Lys Arg Ala Asn Pro Gly Pro Ser Thr Ala Tyr His Ser Ser Ser
305                 310                 315                 320

Gln Cys Ser Thr Asp Leu Asp Leu Asn
                325
```